United States Patent
Ishibashi et al.

(10) Patent No.: US 12,263,317 B2
(45) Date of Patent: Apr. 1, 2025

(54) GUIDE WIRE SHAPING MOLD AND METHOD FOR SHAPING GUIDE WIRE

(71) Applicants: ST. MARIANNA UNIVERSITY SCHOOL OF MEDICINE, Kawasaki (JP); OZK CO., LTD., Yao (JP); SHINWA SYOJI CO., LTD., Higashiosaka (JP)

(72) Inventors: Yuki Ishibashi, Kawasaki (JP); Yoshihiro Akashi, Kawasaki (JP); Haruhiko Yamasaki, Yao (JP); Katsunori Mitsuhashi, Yao (JP); Yoshiro Morishita, Higashiosaka (JP)

(73) Assignees: ST. MARIANNA UNIVERSITY SCHOOL OF MEDICINE, Kawasaki (JP); OZK CO., LTD., Yao (JP); SHINWA SYOJI CO., LTD., Higashosaka (JP)

( * ) Notice: Subject to any disclaimer, the term of this patent is extended or adjusted under 35 U.S.C. 154(b) by 716 days.

(21) Appl. No.: 17/621,666

(22) PCT Filed: Jul. 17, 2020

(86) PCT No.: PCT/JP2020/027748
§ 371 (c)(1),
(2) Date: Dec. 21, 2021

(87) PCT Pub. No.: WO2021/015103
PCT Pub. Date: Jan. 28, 2021

(65) Prior Publication Data
US 2022/0347438 A1    Nov. 3, 2022

(30) Foreign Application Priority Data
Jul. 25, 2019    (JP) .................................. 2019-136519

(51) Int. Cl.
*B21C 3/02*    (2006.01)
*A61M 25/00*    (2006.01)
(Continued)

(52) U.S. Cl.
CPC ........ *A61M 25/09* (2013.01); *A61M 25/0043* (2013.01); *A61M 25/0068* (2013.01);
(Continued)

(58) Field of Classification Search
CPC .. A61M 2025/09108; B21C 3/02; B21C 3/04; B21F 1/06; B21F 45/008;
(Continued)

(56) References Cited

U.S. PATENT DOCUMENTS
1,578,462 A    3/1926 Myers

FOREIGN PATENT DOCUMENTS
JP    H02151328 A    6/1990
JP    H04108555 U    9/1992
(Continued)

OTHER PUBLICATIONS

International Search Report (ISR) mailed Aug. 18, 2020, issued for International application No. PCT/JP2020/027748. (3 pages).
(Continued)

*Primary Examiner* — Leo B Tentoni
(74) *Attorney, Agent, or Firm* — Law Office of Katsuhiro Arai

(57) ABSTRACT

To provide a guide wire shaping mold that reduces damage to a blood vessel by folding back a tip end of the guide wire and do not require heating treatment, and a guide wire shaping method using the guide wire shaping mold. A guide wire shaping mold configured to shaping by reducing an annular diameter of the guide wire in which a tip end is annularly arranged, the guide wire shaping mold includes a wire shaping portion configured such that an annular portion
(Continued)

of the guide wire is arranged, and a wire drawing path formed in a passage way shape, communicating with the wire shaping portion, and configured to retract the guide wire in a linear direction and in a base end direction.

12 Claims, 21 Drawing Sheets

(51) Int. Cl.
*A61M 25/09* (2006.01)
*B21C 3/04* (2006.01)
*B21F 1/06* (2006.01)
*B21F 45/00* (2006.01)
*B29C 33/38* (2006.01)
*B29C 53/02* (2006.01)
*B29C 53/80* (2006.01)
*B29C 53/82* (2006.01)

(52) U.S. Cl.
CPC ......... *A61M 25/008* (2013.01); *B21F 45/008* (2013.01); *B29C 33/3842* (2013.01); *A61M 2025/09108* (2013.01)

(58) Field of Classification Search
CPC ..... B29C 33/3842; B29C 53/02; B29C 53/80; B29C 53/82
USPC ........ 264/219, 280, 285, 339; 425/175, 391; 140/80, 102, 102.5, 104
See application file for complete search history.

(56) References Cited

FOREIGN PATENT DOCUMENTS

| | | |
|---|---|---|
| JP | H07255856 A | 10/1995 |
| JP | H08132164 A | 5/1996 |
| JP | 2006334321 A | 12/2006 |

OTHER PUBLICATIONS

A Notice of Reasons for Refusal issued by the Japanese Patent Office, mailed Dec. 12, 2023, for Japanese counterpart application No. 2021-533992. (2 pages).

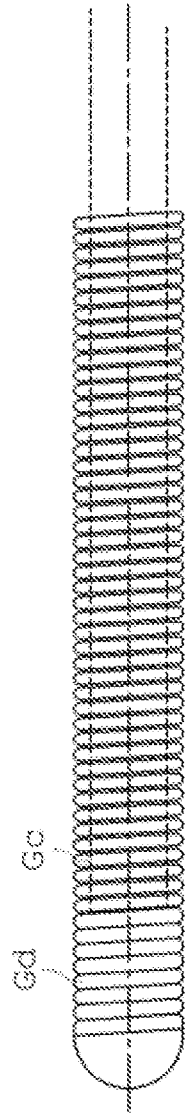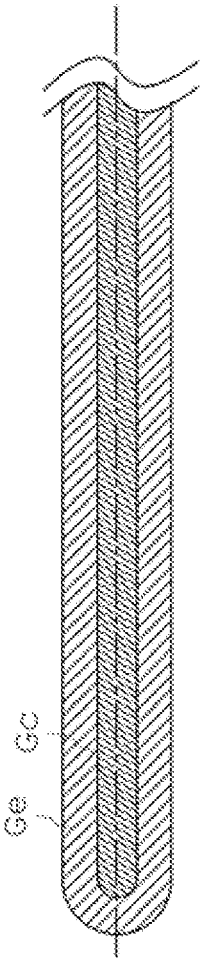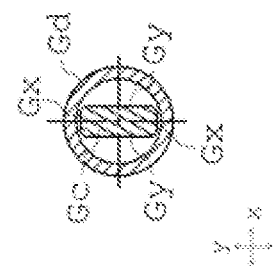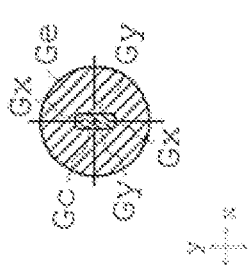
Fig. 4A
Fig. 4B

```
Mold preparation process
112,122,132,142,152,162
```

```
Wire arrangement process
113,123,133,143,153,163

Wire insertion step
    113a,123a,133a,143a,153a,163a

Wire reinsertion step
    113b,123b,133b,143b,153b,163b

Wire arrangement step
    113c,123c,133c,143c,153c,163c
```

```
Annular diameter reduction
process
114,124,134,144,154,164
```

```
Wire taking-out process
115,125,135,145,155,165
```

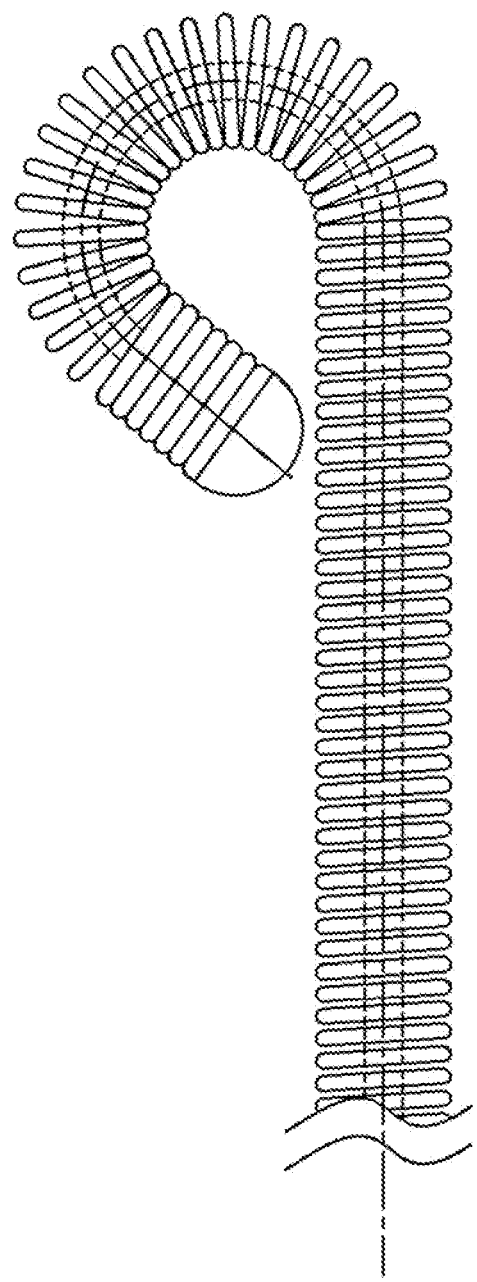

Fig.15
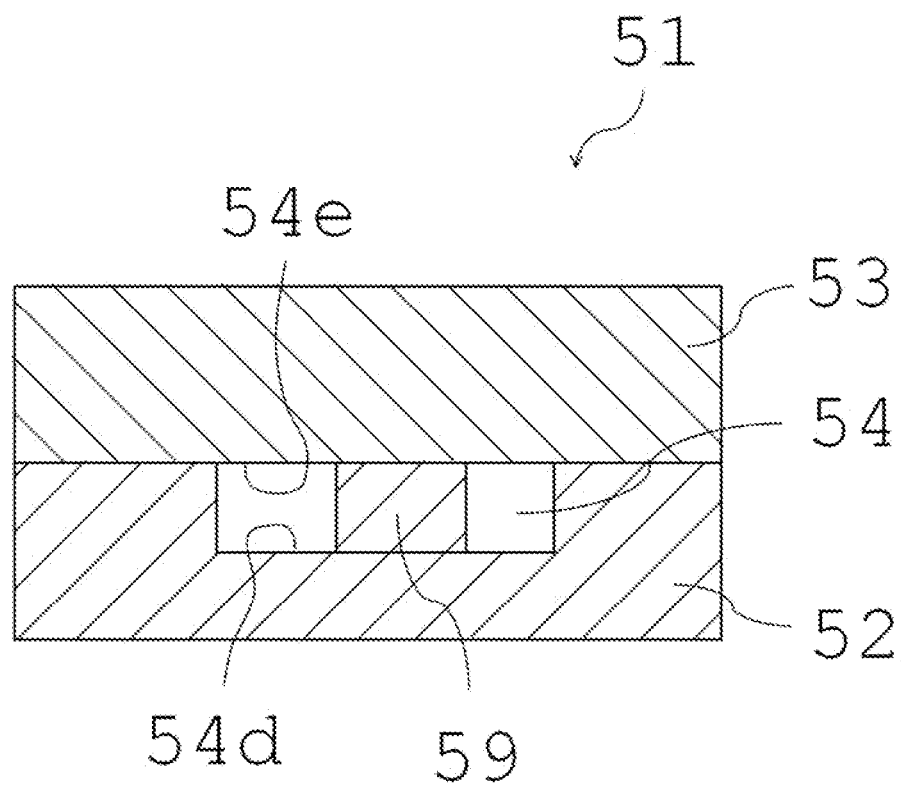
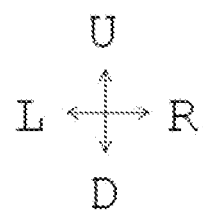

Fig.18A
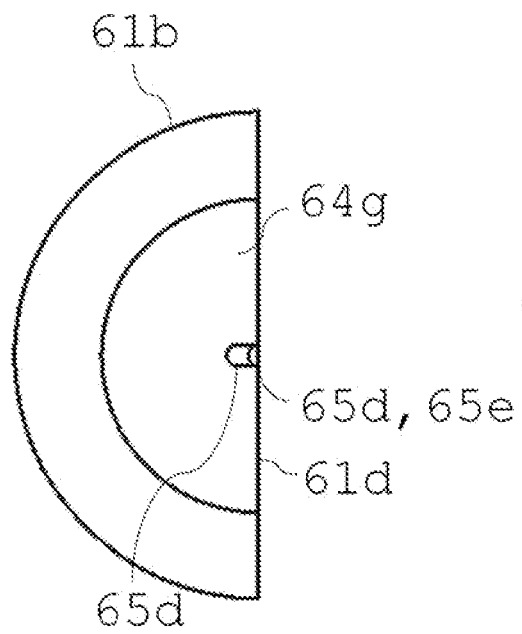
Fig.18B
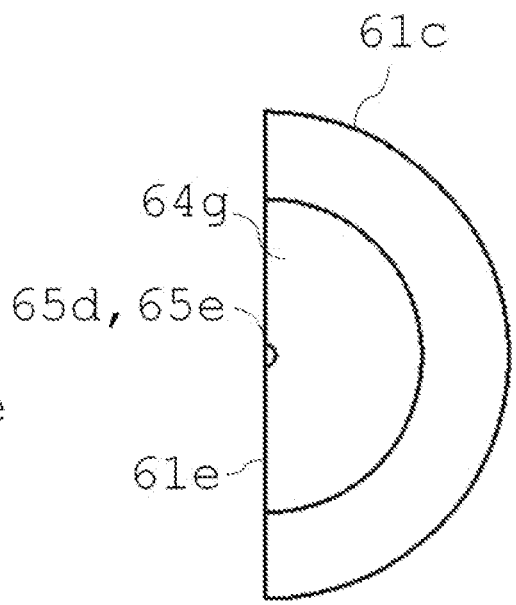
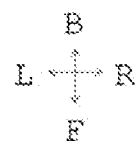
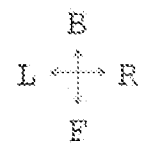

Prior Art       Fig.21
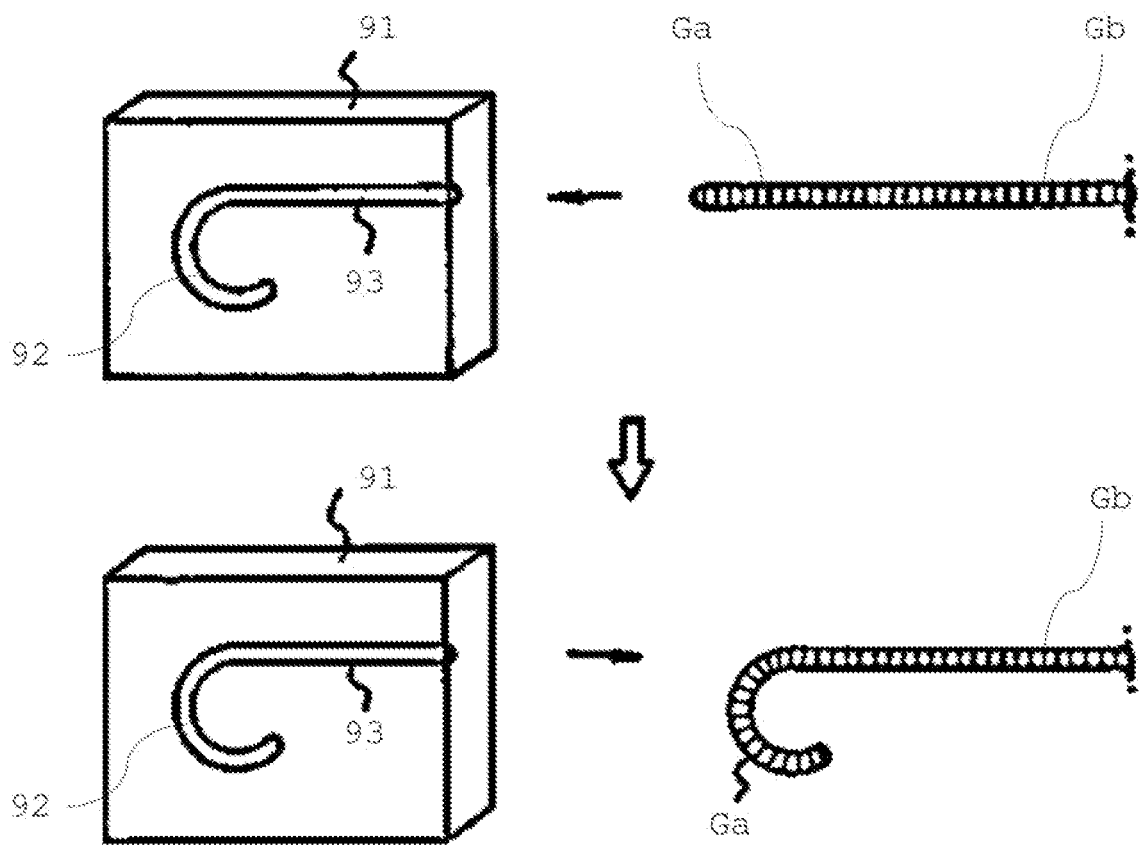

GUIDE WIRE SHAPING MOLD AND METHOD FOR SHAPING GUIDE WIRE

CROSS-REFERENCE TO RELATED APPLICATIONS

This application is the U.S. National Phase under 35 U.S.C. § 371 of International Application PCT/JP2020/027748, filed Jul. 17, 2020, which claims priority to Japanese Patent Application No. JP2019-136519, filed Jul. 25, 2019. The International Application was published under PCT Article 21(2) in a language other than English.

TECHNICAL FIELD

The present invention relates to a guide wire shaping mold and a guide wire shaping method, and particularly, to a guide wire shaping mold having a wire shaping portion in which one end side of a guide wire is annularly arranged and a guide wire shaping method including a mold preparation process of preparing the guide wire shaping mold.

BACKGROUND ART

Conventionally, there is a guide wire shaping mold including a wire shaping portion in which one end side of a guide wire is annularly arranged and a wire drawing path in which the other end side of the guide wire is linearly arranged, in which the wire drawing path is formed in a shape of a passage way and is configured to communicate with a mold outside (Patent Literature 1).

The guide wire refers to a flexible, wire-like instrument for facilitating insertion and indwelling of a catheter introducer into a blood vessel. At the end of the guide wire, there are a patient-side end, which is the guide wire end on the side to be inserted into the patient, and a hand end, which is the guide wire end on the side of the operator who operates. The guide wire bends and deforms the patient-side end, for example, and shapes it in a desired orientation, inclination, and the like, thereby facilitating access to a bend lesion or a side branch.

At this time, a sharp patient-side end possibly damages the inner wall of the blood vessel and, in the worst case, destroys the blood vessel. Therefore, it is required to reduce the damage on the blood vessel by, for example, annularly shaping the patient-side end and folding back the tip end.

The conventional guide wire shaping mold is configured by a mold 91 shown in FIG. 21. The conventional guide wire shaping method includes a heating treatment process of inserting a guide wire G into recess portions 92 and 93 of the mold 91 to hold the shape, putting the guide wire G into a heating furnace, and performing heating treatment preferably at 400 to 600° C. for 30 to 300 minutes. The recess portions 92 and 93 have a wire shaping portion 92 in which one end side Ga of the guide wire G is annularly arranged and a wire drawing path 93 in which the other end side Gb of the guide wire G is linearly arranged. When the guide wire G is taken out from the mold 91, the guide wire G is bent and formed into a shape in which the one end side Ga is held by the mold 91.

At this time, the one end side Ga corresponds to a side to be inserted into the patient.

In the conventional guide wire shaping mold, the one end side Ga of the guide wire G is annularly shaped following the shape of the inside of the wire shaping portion 92, thereby making a shape that can reduce damage on the blood vessel.

CITATIONS LIST

Patent Literature

Patent Literature 1: Japanese Patent Application Laid-Open No. H7-255856

SUMMARY OF INVENTION

Technical Problems

The conventional guide wire shaping mold shapes the guide wire G by performing heating treatment in a heating furnace. The guide wire G is shaped and processed by an operator such as a medical worker at a medical site such as an operating room. At this time, installing a heating furnace that rises high in temperature at a medical site is likely to adversely effect other medical equipment. When the operator operates such a heating furnace, there is a risk that the operator who is about to perform a medical practice is burned.

In view of such a problem, an object of the present invention is to provide a guide wire shaping mold and a guide wire shaping method that reduce damage to a blood vessel by folding back a tip end of the guide wire and do not require heating treatment.

Solutions to Problems (1) The present invention provides a guide wire shaping mold configured to shape a guide wire by reducing an annular diameter of the guide wire in which a tip end is annularly arranged, the guide wire shaping mold including a wire shaping portion configured such that an annular portion of the guide wire is arranged, and a wire drawing path formed in a passage way shape, communicating with the wire shaping portion, and configured to retract the guide wire in a linear direction and in a base end direction.

That is, in the guide wire shaping mold of the present invention, the base end side of the guide wire is retracted via the wire drawing path, whereby the guide wire is pulled in the wire shaping portion, the entire circumference thereof is shortened, and the annular diameter of the annular portion on the side close to the tip end can be reduced.

At this time, in a process of reducing the annular diameter, the annular portion is rounded small, and tension from the base end side is applied in a rounded state to cause plastic deformation. Due to this, the guide wire is removed from the guide wire shaping mold, and the annular portion is shaped to a shape having a desired annular diameter even after removed from the wire shaping portion, and so-called spring back, in which the annular diameter expands again, will not largely occur.

Thus, the annular portion corresponding to the patient side of the guide wire can be shaped to a required size. Since the tip end is folded back, it is possible to reduce damage on the blood vessel caused by the tip end. Note that the annular portion is sometimes referred to as "one end side" in the present description, and the base end side is sometimes referred to as "other end side" in the present description.

Moreover, since the guide wire shaping mold of the present invention enables shaping by plastic deformation as described above, the guide wire shaping mold does not require a heating treatment using a heating furnace and the like.

(2) At least a part of the constituent members may be made of a synthetic resin.

That is, in the guide wire shaping mold of the present invention, since a part or the whole of a portion touched by the guide wire is formed of a synthetic resin, the member can be manufactured in large quantities in a short time by a device such as an injection molding machine. Therefore, it is possible to more economically manufacture the guide wire shaping mold, and eventually, it is possible to economically shape the guide wire. Because of the synthetic resin, it is possible to obtain a guide wire shaping mold that is lighter in weight than a mold made of metal or the like.

The conventional guide wire shaping mold performs guide wire shaping by heating treatment. Therefore, if a member or the like forming the inside of the wire shaping portion, for example, is formed of a synthetic resin, such a member may be deformed or altered due to an increase in temperature, and it has not been possible to adopt a synthetic resin as a material.

(3) The wire shaping portion may be configured by a wire shaping chamber that forms a flat cavity wider than the width of the wire drawing path.

That is, since this wire shaping chamber is formed in a flat cavity wider than the width of the wire drawing path, the annular diameter after reduction can be discretionarily determined due to the length of drawing the base end side with respect to the annular portion of the guide wire extending in this cavity.

(4) In the wire shaping chamber, a part of an inner wall may constitute a wire planar guide wall having a substantially planar shape, and the wire planar guide wall and a passage wall of the wire drawing path may be continuous in a same plane shape.

That is, since the wire shaping chamber has the wire planar guide wall, and the wire drawing path is continuous in the same plane shape from this wire planar guide wall, the guide wire is restricted from deforming out of the same plane except for the annular portion in the process of reducing the annular diameter. Therefore, while the annular portion of the guide wire remains in the cavity, portions along the wire planar guide wall and the wire drawing path are maintained in a substantially linear state. As a result, the guide wire exhibits a posture such as a p shape, a q shape, a b shape, and a d shape of lower case alphabets in plan view, and portions corresponding to the respective vertical bars are maintained in a linear state.

Incidentally, there is a known case where it is somewhat difficult for the operator to discretionarily shape the orientation, inclination, and the like of the guide wire for access to a bend lesion or a side branch when the guide wire does not maintain the linear state and just bends such that the tip end of the p shape vertical bar greatly inclines leftward as it goes downward, and bends such that the tip end of the q shape vertical bar greatly inclines rightward as it goes downward. In such a case, the operator finds it preferable that the vertical bar of the p shape or the q shape maintains in the linear state as described above.

Thus, in the guide wire shaping mold of the present invention, the tip end of the guide wire can be folded back, and the guide wire can be processed into a state where the operator easily shapes the guide wire.

(5) In the wire shaping chamber, a part of an inner wall may constitute a wire curved surface guide wall having a curved surface shape, and the wire curved surface guide wall and a passage wall of the wire drawing path may be continuous on a side opposite to a side continuous in the same plane shape.

In the process of reducing the annular diameter, a tip end of the guide wire or a portion close to the tip end abuts on the wire curved surface guide wall.

At this time, meanwhile portions corresponding to the vertical bar of the p shape or the q shape are drawn out toward the mold outside, portions corresponding to the ring of the p shape or the q shape receives frictional force from the wire curved surface guide wall, and remains in the wire shaping chamber while being in an annular state, thereby continuously reducing the annular diameter.

Thus, the guide wire shaping mold of the present invention can reliably turn back the tip end of the guide wire without performing heating treatment.

(6) The wire shaping chamber may have a projection wire guide shaft in which any or both of a pair of inner walls facing each other in a thickness direction of the flat shape are provided in the thickness direction.

That is, since the wire shaping chamber has the projection wire guide shaft, the annular portion of the guide wire can be bent and deformed so as to be wound around the projection wire guide shaft. Therefore, the operator can easily reduce the annular diameter, and to perform more efficient shaping of the guide wire.

(7) The wire shaping chamber may have a columnar wire guide shaft connected to both of a pair of inner walls facing each other in a thickness direction of the flat shape.

That is, since the wire shaping chamber has the columnar wire guide shaft, the annular portion of the guide wire can be bent and deformed so as to be wound around the columnar wire guide shaft. Therefore, the operator can easily reduce the annular diameter, and to perform more efficient shaping of the guide wire.

(8) The guide wire shaping mold includes a main body portion on one side and a lid portion on the other side configured to cover the main body portion, into which the guide wire shaping mold is divided into two in a thickness direction of a flat shape of the wire shaping chamber, and a part of a bottom surface of the lid portion may form a ceiling of the wire shaping chamber.

That is, when the guide wire is shaped, the main body portion is covered with the lid portion, and the guide wire can be bent and deformed in the wire shaping chamber. On the other hand, after shaped, the lid portion is opened to release the ceiling of the wire shaping chamber, and the guide wire after the shaping can be taken out from the wire shaping chamber. By opening and closing such the lid portion, one guide wire can be shaped, and subsequently, another guide wire can be efficiently shaped.

(9) The wire shaping portion may have an inner peripheral surface of a truncated cone shape, and the wire drawing path may communicate with the wire shaping portion at a tip end portion of the truncated cone shape.

The tip end portion of the guide wire is known to have a substantially rectangular transverse cross-sectional shape of a core wire provided inside the guide wire. Therefore, the transverse cross section has a long side in the y direction, for example, and a short side in the x direction forming 90° with the y direction.

It is known that bending rigidity at the time of displacing the guide wire in the y direction of the long side direction is larger than bending rigidity at the time of displacing the guide wire in the x direction, for example, when bending rigidity, which is the magnitude of resistance with respect to deformation, is compared with each other between a case of bending the guide wire such that one end is displaced in the y direction and a case of bending the guide wire such that one end is displaced in the x direction. On the contrary, it is known that bending rigidity at the time of displacing the guide wire in the x direction of the short side direction is smaller.

In this situation, in order to reduce the annular diameter of the guide wire having such a bending characteristic, the inventor has found that when the annular portion is shaped to be small using the guide wire shaping mold of the present invention, the guide wire changes its posture by itself, and the relationship between the long side in the y direction of the core wire and the inner peripheral surface of a truncated cone shape of the wire shaping portion converges to a relationship of positions parallel to each other. When the y direction long side and the inner peripheral surface are parallel to each other as described above, the guide wire is bent in the x direction, and thus the bending rigidity is relatively small. As a result, according to the guide wire shaping mold of the present invention, the guide wire can take a posture with lower bending rigidity by itself when being bent for shaping. Therefore, the operator can shape the guide wire by applying a smaller force.

By this action, the operator can reduce the annular diameter in a posture in which the bending rigidity of the guide wire is smaller, that is, a posture in which the guide wire is more easily bent. Therefore, the operator can easily shape the guide wire by the guide wire shaping mold.

(10) In the wire drawing path, a cross section of a shaping portion adjacent portion, which is a portion adjacent to the wire shaping portion, may have a shape and an area in which two of the guide wires can be arranged in an overlapping manner, the wire drawing path may have has the shaping portion adjacent portion and a wire drawing portion, which is a portion continuous with the shaping portion adjacent portion in an orientation away from the wire shaping portion and having a cross-sectional area smaller than a cross-sectional area of the shaping portion adjacent portion, and may have a step surface facing an orientation approaching the wire shaping portion in a step between the shaping portion adjacent portion and the wire drawing portion.

That is, in the guide wire shaping mold of the present invention, since the wire drawing path allows two guide wires to be arranged in an overlapping manner at a shaping portion adjacent portion and has a step surface at the step between the shaping portion adjacent portion and the wire drawing portion, the operator can insert a most tip end portion of the guide wire into the shaping portion adjacent portion and stop insertion in a state where the most tip end portion abuts on the step surface. Therefore, the operator can fix the most tip end portion to the wire drawing path and annularly arrange and shape the tip end with ease.

(11) The present invention provides a guide wire shaping method including: a mold preparation process of preparing a guide wire shaping mold including a wire drawing path formed in a passage shape and a wire shaping portion including a shaping space that communicates with the wire drawing path; a wire arrangement process of inserting a guide wire from an outlet hole of the wire drawing path and annularly arranging a tip end of the guide wire in the wire shaping portion; and an annular diameter reduction process of drawing out a base end side of the guide wire from the outlet hole and shortening an entire circumference of an annular portion on the tip end side to reduce an annular diameter of the annular portion.

That is, in the guide wire shaping method of the present invention, by reducing the annular diameter of the annular portion of the guide wire, it is possible to shape the guide wire into a shape in which the tip end is reliably folded back.

Thus, it is possible to reduce damage on the blood vessel caused by the tip end of the guide wire.

Moreover, since the guide wire shaping method of the present invention enables plastic deformation in the annular diameter reduction process, the guide wire shaping method does not require a heating treatment using a heating furnace and the like.

(12) In the guide wire shaping mold prepared in the mold preparation process, the wire shaping portion is opened to a wire outside of the guide wire shaping mold, and the wire arrangement process may include a wire insertion step of causing a tip end of the guide wire inserted from the outlet hole to protrude to the mold outside through the wire shaping portion, and a wire reinsertion step, which is a step of reversing an orientation and returning to the wire shaping portion again.

That is, by including the wire insertion step and the wire reinsertion step, it is possible to easily arrange the guide wire at a predetermined position of the guide wire shaping mold, for example, without disassembling the guide wire shaping mold and arranging the guide wire, and it is possible to shape the guide wire more efficiently.

Advantageous Effects of Invention

Thus, the present invention provides a guide wire shaping mold and a guide wire shaping method that reduce damage to a blood vessel by folding back a tip end of the guide wire and do not require heating treatment.

BRIEF DESCRIPTION OF DRAWINGS

FIG. 4A shows a transverse cross section of a guide wire with a safety wire on the left side and shows a side view thereof on the right side. FIG. 4B shows a transverse cross-sectional view of a guide wire with a plastic jacket on the left side and shows a side cross-sectional view thereof on the right side.

FIG. 6 shows a flowchart presenting a guide wire shaping method of the present invention.

FIG. 10 shows an example of a guide wire after shaping.

FIG. 15 shows a cross-sectional front view of a guide wire shaping mold according to a fifth embodiment of the present invention.

FIG. 18A shows a front view of a first guide wire shaping mold block according to the sixth embodiment of the present invention. FIG. 18B shows a front view of a second guide wire shaping mold block of the same.

FIG. 21 is an explanatory view of a mold 91, which is a conventional guide wire shaping mold.

DESCRIPTION OF EMBODIMENTS

The first embodiment of the present invention will be described with reference to FIGS. 1 to 10. In FIGS. 1A to D and FIG. 2, 1 is a guide wire shaping mold, and this guide wire shaping mold 1 includes a main body portion 2 and a lid portion 3.

Figure 1A:
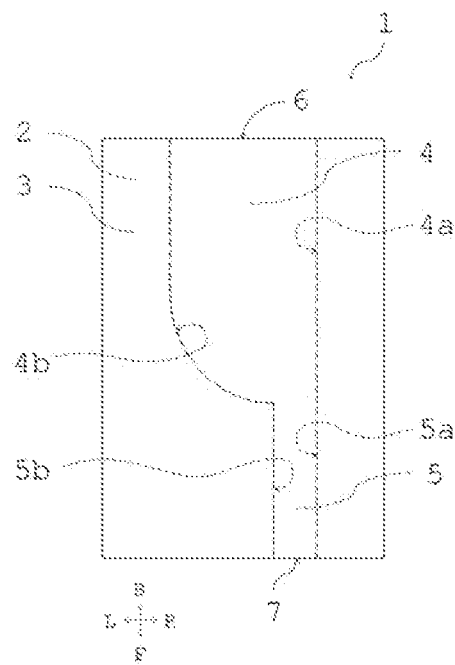
FIG. 1A shows a plan view of a guide wire shaping mold according to a first embodiment of the present invention.
Figure 1C:
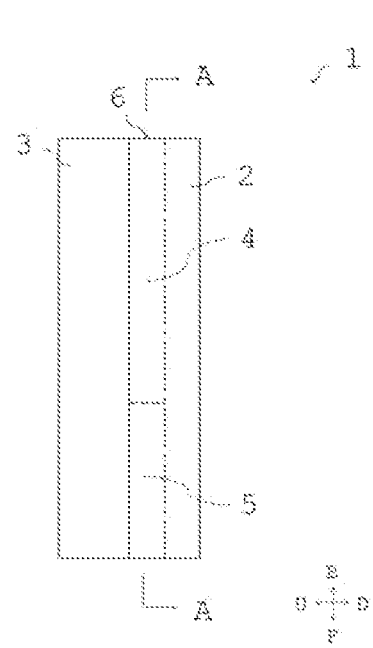
FIG. 1C shows a right side view of the same.
Figure 1B:
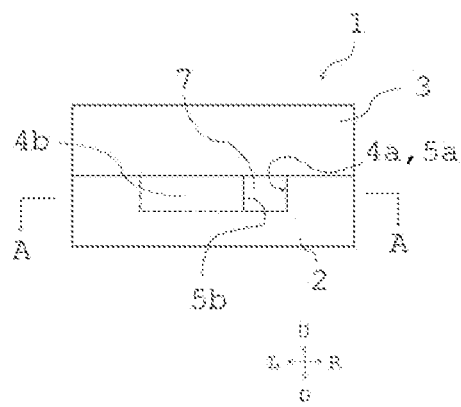
FIG. 1B shows a front view of the same.
Figure 1D:
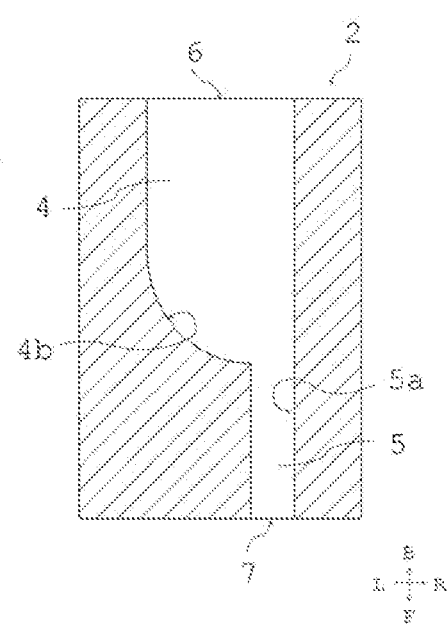
FIG. 1D shows a plan cross-sectional view of a main body portion of the guide wire shaping mold.

In FIG. 1A, which is a plan view, an arrow F represents the forward orientation in a front-rear direction of the guide wire shaping mold 1. An arrow B represents the rearward orientation in the front-rear direction. The forward side is referred to as a front side, and the rearward side is referred to as a rear side. An arrow L represents a leftward orientation L in a left-right direction. An arrow R represents a rightward orientation R in the left-right direction. The leftward side is referred to as a left side, and the rightward side is referred to as a right side. In FIG. 1B, which is a front view, in FIG. 1C, which is a right side view, and in FIG. 2, which is a rear view, an arrow U represents an upward orientation in an up-down direction of the guide wire shaping mold 1. An arrow D represents a downward orientation in the up-down direction. The upward side is referred to as an up side, and the downward side is referred to as a down side. The same applies to other figures.

The guide wire shaping mold 1 forms a rectangular parallelepiped. The main body portion 2 and the lid portion 3 also form a rectangular parallelepiped, and the lid portion 3 overlaps the main body portion 2 so as to be arranged on the up side of the main body portion 2. Note that in order to simply show the structure of the guide wire shaping mold 1, the entire guide wire shaping mold 1, the main body portion 2, and the lid portion 3 are expressed in a rectangular parallelepiped shape, but the entire guide wire shaping mold 1, the main body portion 2, or the lid portion 3 may have a shape other than the rectangular parallelepiped shape as long as the shape and arrangement of a wire shaping chamber 4 and a wire drawing path 5 as described below are as shown in these figures.

The main body portion 2 and the lid portion 3 are formed by, for example, injection molding with synthetic resins such as an acrylic resin and polycarbonate, respectively, as raw materials. The main body portion 2 and the lid portion 3 are detachably assembled by a screw in an up-down direction not illustrated. In an assembled state, the main body portion 2 and the lid portion 3 are in close contact with an up side surface of the main body portion 2 and a down side surface of the lid portion 3 in the up-down direction, except for the place where the wire shaping chamber 4 and the wire drawing path 5 described below are arranged.

Figure 2:
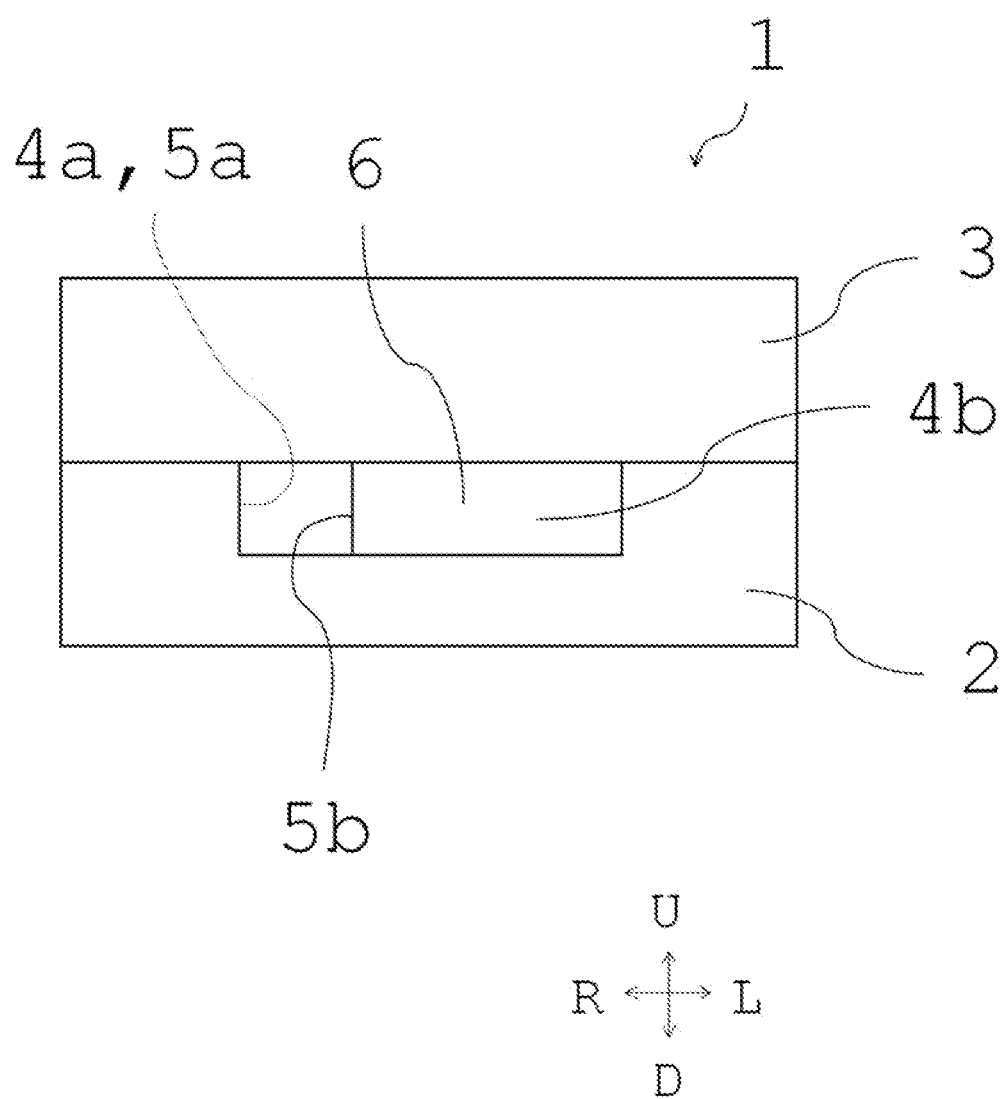
FIG. 2 shows a rear view of the guide wire shaping mold according to the first embodiment of the present invention.

As shown in FIGS. 1 and 2, the main body portion 2 has the recessed wire shaping chamber 4 and the wire drawing path 5 provided downward from the up side surface. In a state where the lid portion 3 is assembled to the main body portion 2, the wire shaping chamber 4 forms a flat cavity, and the wire drawing path 5 forms a passage. In the left-right direction, the width of the wire shaping chamber 4 is larger than the width of the wire drawing path 5. The wire shaping chamber 4 and the wire drawing path 5 communicate with each other in the front-rear direction. FIG. 1D shows an A-A cross-sectional view of the main body portion 2 in which the viewing orientation is designated by the cross-section designation line of FIGS. 1B and 1C.

In the state where the lid portion 3 is assembled to the main body portion 2, a part of the bottom surface of the lid portion 3 forms a ceiling of each of the wire shaping chamber 4 and the wire drawing path 5. The wire shaping chamber 4 forms a rearward opening outlet slit 6 and opens to the mold outside via the outlet slit 6. In the state where the lid portion 3 is assembled to the main body portion 2, the wire drawing path 5 forms a forward opening outlet hole 7 and communicates with a mold outside via the outlet hole 7.

Note that the wire shaping chamber 4 is sometimes referred to as a "wire shaping portion" in the present description.

The wire shaping chamber 4 has a leftward facing inner wall in the cavity. This inner wall is represented by a straight line in the front-rear direction in plan view of FIGS. 1A and 1D, and is referred to as a wire planar guide wall 4a.

The wire shaping chamber 4 has a substantially rightward facing inner wall in the cavity. The rear portion of this inner wall is represented by a straight line in the front-rear direction in plan view similarly, and the front portion is represented by a substantial arc curved line having the center inside the wire shaping chamber 4. This curved portion represented by the curved line is referred to as a wire curved surface wall 4b. The wire curved surface wall 4b faces substantially the left-right direction at the terminal end of the front portion because it is an arc in plan view.

The wire drawing path 5 has a leftward facing inner wall. This inner wall is represented by a straight line in the front-rear direction in plan view of FIGS. 1A and 1D and is referred to as a wire planar guide extension wall 5a. The wire planar guide extension wall 5a is continuous with the wire planar guide wall 4a on the same plane in the front-rear direction.

The wire drawing path 5 has a rightward facing inner wall. This inner wall is represented by a straight line in the front-rear direction in plan view and is referred to as a wire curved surface adjacent wall 5b. The wire curved surface adjacent wall 5b is located on the opposite side of the wire planar guide extension wall 5a with respect to the center line of the wire drawing path 5. The wire curved surface adjacent wall 5b is continuous with the wire curved surface wall 4b in a substantially right angle in plan view.

Figure 3A:
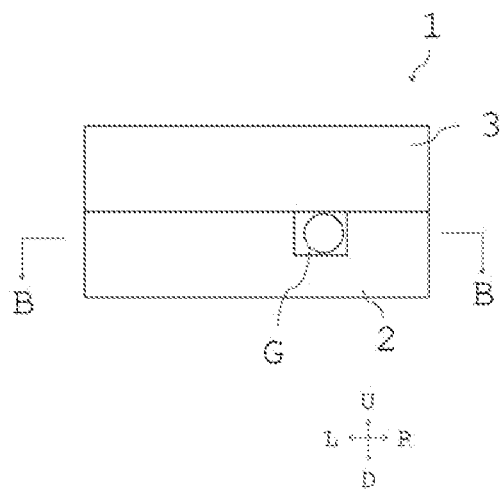
FIG. 3A shows a plan view of the guide wire shaping mold in a state where a guide wire according to the first embodiment of the present invention is arranged.
Figure 3B:
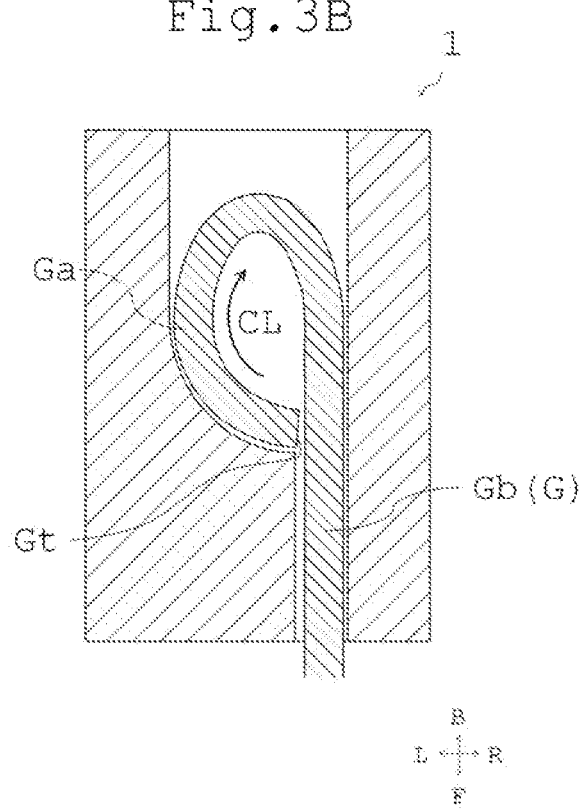
FIG. 3B shows a plan cross-sectional view of the same.

FIGS. 3A and 3B show a state where the guide wire G is arranged in the guide wire shaping mold 1. FIG. 3A shows a front view of the guide wire shaping mold 1, and FIG. 3B shows a B-B cross-sectional view of the main body portion 2 and the guide wire G in which the viewing orientation is designated by the cross-section designation line of FIG. 3A.

In a case of a blood vessel guide wire, for example, the guide wire G includes members such as a safety wire, a core wire, a coil, or a plastic jacket, depending on the type as shown in Japanese Industrial Standard JIST3267:2017. On the other hand, in the present description and each figure, expressions of these configurations are simplified and expressed in line shapes.

FIGS. 4A and 4B are detailed views showing an example of the guide wire G. FIG. 4A shows a transverse cross section of the guide wire with a safety wire shown on the left side, and shows a side view thereof on the right side. FIG. 4B shows a transverse cross section of the guide wire with a plastic jacket on the left side, and shows a side cross-sectional view thereof on the right side.

The guide wire G has a substantially rightward facing most tip end portion Gt in FIG. 3B. This most tip end portion Gt is a patient-side end, and an annular portion in the figure including the most tip end portion Gt is hereinafter referred to as "one end side (Ga)". The one end side Ga corresponds to a side to be inserted into the patient.

On the other hand, the opposite side to the most tip end portion Gt is a hand end and is located on the down side of the figure, but the hand end side is omitted from the middle in each figure. A portion closer to the hand end than the one end side Ga is hereinafter referred to as "other end side (Gb)".

The one end side Ga is annularly arranged in the wire shaping chamber 4 as shown in FIG. 3B. The other end side Gb is linearly arranged in the wire drawing path 5. The one end side Ga forms a curved line in a clockwise direction CL from the most tip end portion Gt in plan view, and the curved state continues up to a point where the guide wire G merges with the wire planar guide wall 4a. The other end side Gb forms a straight line in the front-rear direction in plan view. The straight line state starts from a point where the guide wire G merges with the wire planar guide wall 4a and continues downward.

At this time, the portion from the most tip end portion Gt to the middle of the one end side Ga is along a part of the wire curved surface wall 4b in the wire shaping chamber 4. The other end side Gb is along the wire planar guide wall 4a and the wire planar guide extension wall 5a continuous with this wire planar guide wall 4a in the wire shaping chamber 4 and in the wire drawing path 5.

Figure 5A:
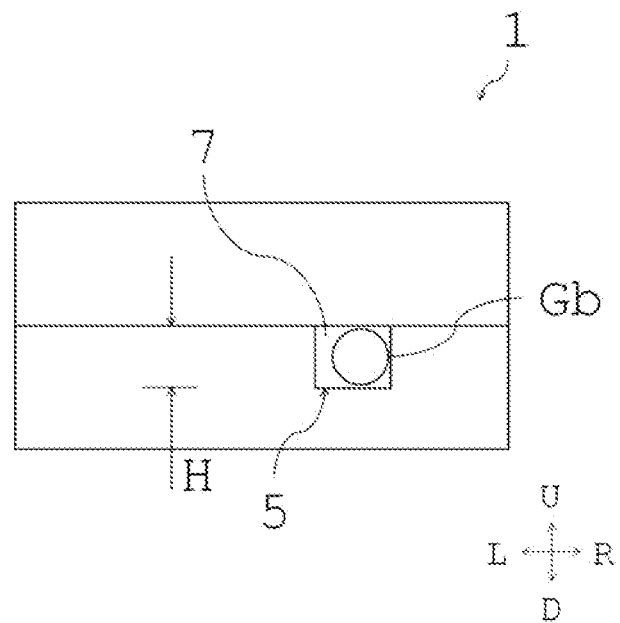
FIG. 5A shows a plan view of the guide wire shaping mold in a state where the guide wire according to the first embodiment of the present invention is arranged.
Figure 5B:
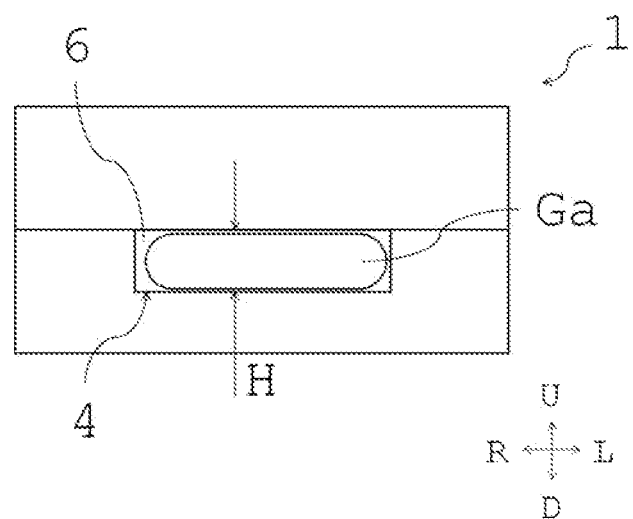
FIG. 5B shows a rear view of the same.

FIGS. 5A and 5B show a front view and a rear view, respectively, in a state where the guide wire G is arranged in the guide wire shaping mold 1. FIG. 5A shows a state where the other end side Gb protrudes forward from the outlet hole 7, and FIG. 5B shows a state where the one end side Ga is seen from the outlet slit 6. As shown in FIGS. 5A and 5B, a height H of the wire shaping chamber 4 and the wire drawing path 5 in the up-down direction is set slightly larger than the outer diameter of the guide wire G.

Here, a guide wire shaping method 111 including a procedure of shaping the guide wire G will be described. The guide wire shaping method 111 is shown in the flowchart of FIG. 6.

The guide wire shaping method 111 includes a mold preparation process 112 of preparing the guide wire shaping mold 1 first. In the mold preparation process 112, the guide wire shaping mold 1 in a state where the main body portion 2 and the lid portion 3 are assembled with screws in the up-down direction not illustrated is prepared. Then, the operator prepares the guide wire G and the guide wire shaping mold 1 at hand.

After the mold preparation process 112, the guide wire shaping method 111 includes a wire arrangement process 113 of arranging the guide wire G in the guide wire shaping mold 1.

Figure 7A:
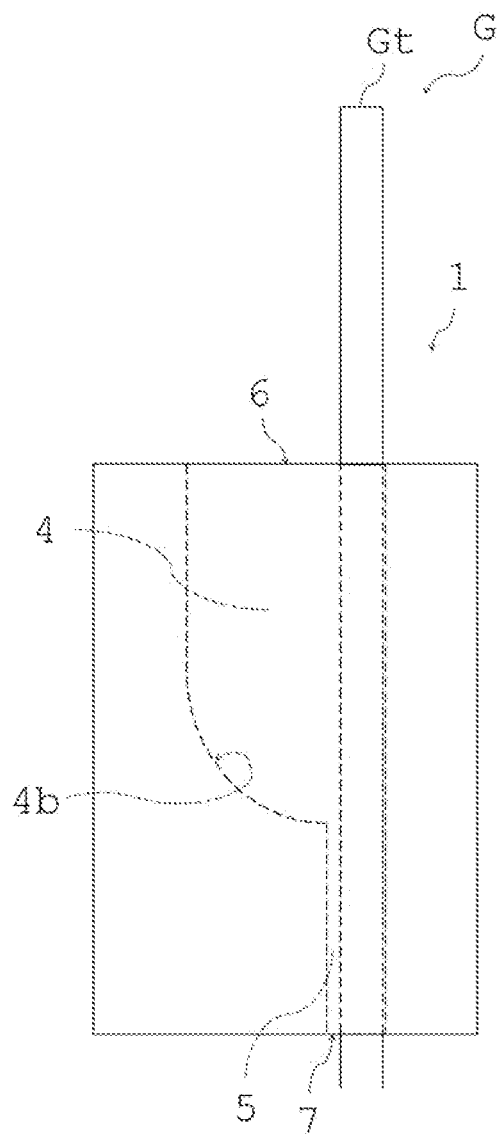
FIGS. 7A and 7B show plan views of a guide wire and a guide wire shaping mold in a guide wire shaping method according to the first embodiment of the present invention.

In the wire arrangement process 113, the operator first inserts the most tip end portion Gt of the guide wire G from the outlet hole 7 using fingers, and sequentially passes upward the most tip end portion Gt through the wire drawing path 5 and the wire shaping chamber 4. This state is shown in FIG. 7A. The most tip end portion Gt protrudes to the mold outside through the outlet slit 6. This step is referred to as a wire insertion step 113a.

Figure 7B:
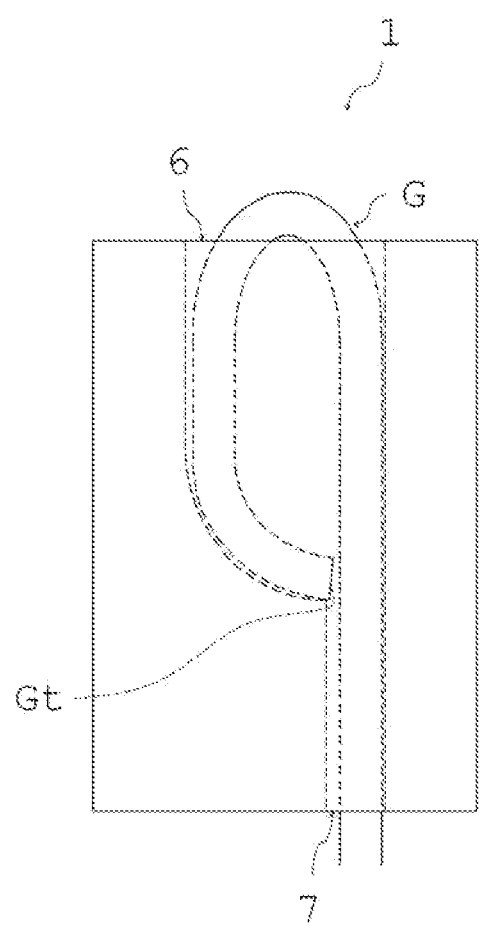

Next, in the wire arrangement process 113, the operator performs an operation of turning the guide wire G counterclockwise using the fingers so as to reverse the orientation of the most tip end portion Gt downward. Then, the operator returns the most tip end portion Gt to the wire shaping chamber 4, and bends and deforms the guide wire G along the wire curved surface wall 4b as shown in FIG. 7B. This step is referred to as a wire reinsertion step 113b.

Next to the wire reinsertion step 113b, in the wire arrangement process 113, the operator pulls the hand side of the guide wire G. As a result, as shown in FIG. 3B, when the other end side Gb of the guide wire G is pulled downward from the large annular state as shown in FIG. 7B, the annular diameter of the guide wire G in this annular state is reduced and changes to a relatively small annular state.

Thus, the one end side Ga of the guide wire G is annularly arranged in the wire shaping chamber 4 as in FIG. 3B, and the other end side Gb is linearly arranged in the wire drawing path 5. This step is referred to as a wire arrangement step 113c.

At this time, since the wire arrangement process 113 includes the wire insertion step 113a and the wire reinsertion step 113b, it is not necessary to disassemble the guide wire shaping mold 1 into the main body portion 2 and the lid portion 3 for arranging the guide wire G, and the guide wire G can be arranged at a predetermined position in a state where the main body portion 2 and the lid portion 3 are assembled. As a result, the guide wire G can be more efficiently shaped.

Figure 8A:
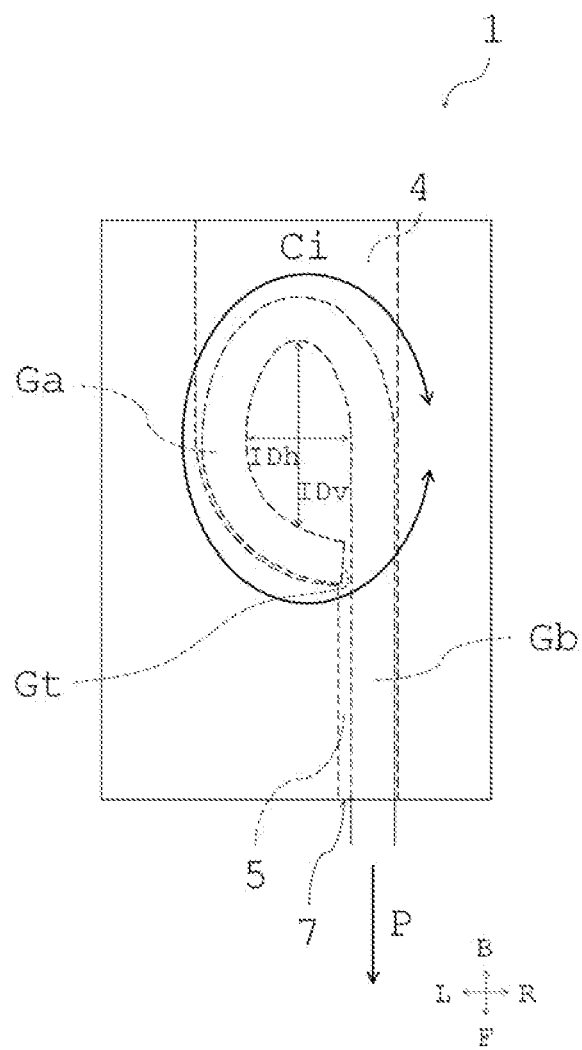
FIGS. 8A and 8B show plan views of a guide wire and a guide wire shaping mold in the guide wire shaping method according to the first embodiment of the present invention.
Figure 8B:
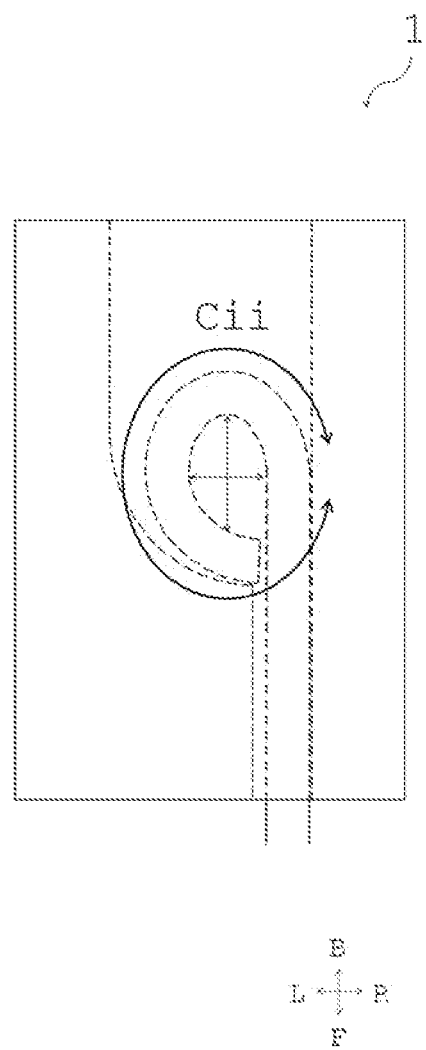

Next to the wire arrangement process 113, the operator further draws out a part of the other end side Gb toward the mold outside as shown in FIGS. 8A and 8B, shortens the entire circumference of the one end side Ga in the annular state, and reduces an annular inner diameter ID of the one end side Ga. At the same time, the annular outer diameter of the one end side Ga is reduced. This process is referred to as an annular diameter reduction process 114.

In the annular diameter reduction process 114, the operator pulls downward the other end side Gb exposed to the mold outside, and draws out a part of the other end side Gb remaining in the wire drawing path 5 toward the mold outside through the outlet hole 7. In this manner, the tensile force when the other end side Gb is pulled downward is indicated by an arrow P according to the orientation of pulling in FIG. 8A.

At this time, since the wire planar guide wall 4a and the wire planar guide extension wall 5a are substantially linearly continuous in the front-rear direction, the one end side Ga and the other end side Gb are restricted from deforming out of this substantially linear shape except for the rounded portion of the one end side Ga. Therefore, while such a rounded portion remains in the cavity of the wire shaping chamber 4, the portion along the wire planar guide wall 4a and the wire drawing path 5 is kept in a linear state.

On the other hand, meanwhile the guide wire G receives the tensile force P, the most tip end portion Gt abutting on the wire curved surface wall 4b or a portion close to the most tip end portion Gt in the one end side Ga receives the frictional force from the wire curved surface wall 4b. As a result, meanwhile the other end side Gb is displaced downward by the tensile force P, the one end side Ga in the annular state remains in the wire shaping chamber 4, and the entire circumference C of the annular shape is shortened. FIGS. 8A and 8B show a state where an entire circumference Cii after pulling by the tensile force P becomes shorter than an entire circumference Ci before pulling.

Since the entire circumference C becomes short in this manner, an annular inner diameter IDv in the front-rear direction and an annular inner diameter IDh in the left-right direction, for example, of the one end side Ga become smaller after pulling than that before pulling. As a result, by reducing the annular inner diameter ID of the one end side Ga as shown in FIG. 8B, plastic deformation occurs in a state where the one end side Ga is rounded small, and the guide wire G can be shaped into a shape reliably folded back without performing heating treatment. The annular outer diameter of the one end side Ga is also reduced accompanying the annular inner diameter. As a result of these, it is possible to reduce damage on the blood vessel caused by the most tip end portion Gt and the one end side Ga.

The operation of reducing the annular diameter of the guide wire G by pulling the guide wire G in the wire arrangement step 113c of the wire arrangement process 113 and the operation of further reducing the annular diameter by further pulling the guide wire G in the annular diameter reduction process 114 may be continuously performed. That is, these two operations can be performed in series although the operation before the one end side Ga and the other end side Gb are arranged in the predetermined shape in FIG. 3B belongs to the wire arrangement process 113 and the operation after the same belongs to the annular diameter reduction process 114.

Next to the annular diameter reduction process 114, in order to remove the lid portion 3 from the main body portion 2, the operator loosens or removes the screw in the up-down direction fastened for joining the main body portion 2 and the lid portion 3 in the mold preparation process 112, thereby disassembling the guide wire shaping mold 1. By removing the lid portion 3 from the state of the front view of FIG. 5A, the rear view of FIG. 5B, and the like in this manner, the ceiling of each of the wire shaping chamber 4 and the wire drawing path 5 is opened, and the portion that was the cavity is exposed upward.

This allows the operator to take out the one end side Ga and the other end side Gb upward from the wire shaping chamber 4 and the wire drawing path 5 using fingers. This process is referred to as a wire taking-out process 115. Then, through the wire taking-out process 115, the operator can insert the shaped guide wire G into the patient from the one end side Ga.

Figure 9C:
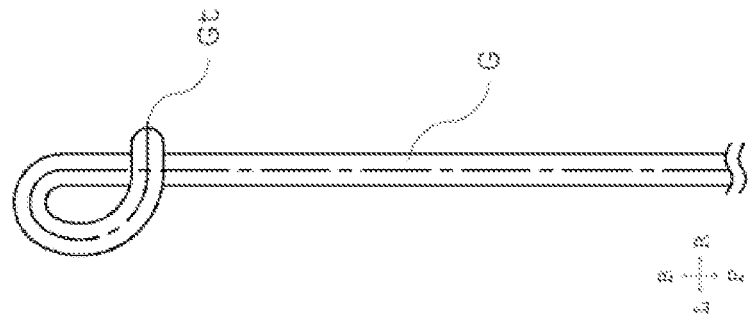
FIGS. 9A, 9B, and 9C show examples of a guide wire after shaping.
Figure 9B:
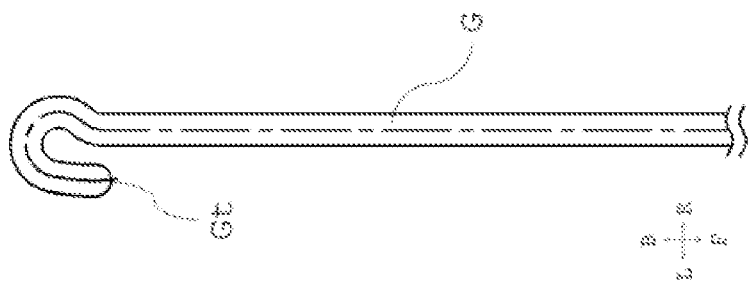
Figure 9A:
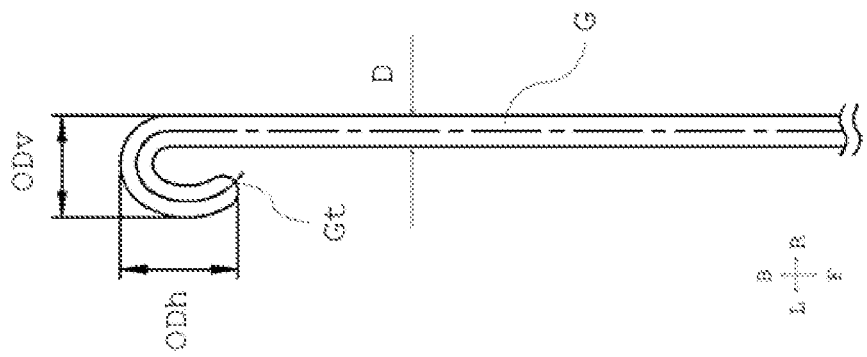

An overview of the shaped guide wire G through the wire taking-out process 115 is shown in FIG. 9A. Through the annular diameter reduction process 114, the guide wire G in a state where the one end side Ga is rounded as shown in FIG. 8B is taken out from the guide wire shaping mold 1, thereby causing slight spring back, but is shaped into a desired shape as shown in FIG. 9A.

As an example, using the guide wire G having an outer diameter D of 0.36 mm shown in FIG. 9A, it is possible to perform shaping in which an annular portion has an annular outer diameter ODh of 1.32 mm in the front-rear direction and an annular outer diameter ODv of 1.15 mm in the left-right direction. As described above, by using the guide wire shaping mold 1 of the present invention and performing the guide wire shaping method 111, it is possible to shape the guide wire G into a desired annular state. Then, since the most tip end portion Gt is folded back, it is possible to reduce damage on the blood vessel caused by the most tip end portion Gt.

Note that, when the guide wire G is shaped to be bent downward D from the annular portion as shown in the comparative example of FIG. 9B, it is known to be somewhat difficult for the operator to discretionarily shape the direction, inclination, and the like of the guide wire G for access to a bend lesion or a side branch. Therefore, there is a case where it is preferable for the operator that the guide wire G is shaped in a posture where the waist extends straight as shown in FIG. 9A.

According to the guide wire shaping mold 1 and the guide wire shaping method 111 of the present invention, since the wire planar guide wall 4a whose outer edge is represented by a straight line in plan view is provided, and the wire drawing path 5 is continued from the wire planar guide wall 4a in a substantially straight line shape, it is possible to shape the straight extending posture as shown in FIG. 9A.

When the guide wire G is shaped into a shape as shown in the comparative example of FIG. 9C, a part of the one end side Ga and a part of the other end side Gb intersect in the up-down direction, and the most tip end portion Gt protrudes to the right side relative to the other end side Gb in plan view, the most tip end portion Gt protrudes and comes into contact with the inner wall of the blood vessel, which may cause damage on the blood vessel.

According to the guide wire shaping mold 1 and the guide wire shaping method 111 of the present invention, the height H of the wire shaping chamber 4 is set to be slightly larger than the outer diameter of the guide wire G as shown in FIGS. 5A and 5B, so that the one end side Ga and the other end side Gb do not intersect in the up-down direction. As a result, the most tip end portion Gt does not protrude rightward relative to the other end side Gb.

As another example, FIG. 10 shows an external view when the guide wire G with a safety wire is shaped.

Note that the wire curved surface wall 4b may be a curved surface other than a substantial arc in plan view if it is a shape with which the one end side Ga can be along.

The terminal end of the front portion may have an inclination to position downward as rightward with respect to the left-right direction, for example, without facing substantially the left-right direction. At this time, the wire curved surface adjacent wall 5b is continuous with the wire curved surface wall 4b at an obtuse angle in plan view.

Figure 11A:
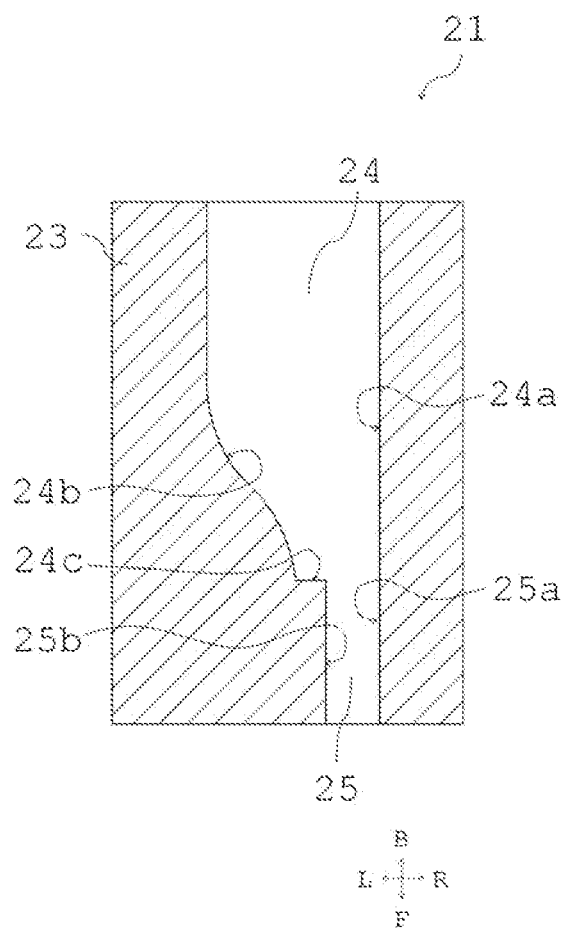
FIGS. 11A and 11B show plan cross-sectional views of a guide wire shaping mold in a state where a guide wire according to a second embodiment of the present invention is arranged.
Figure 11B:
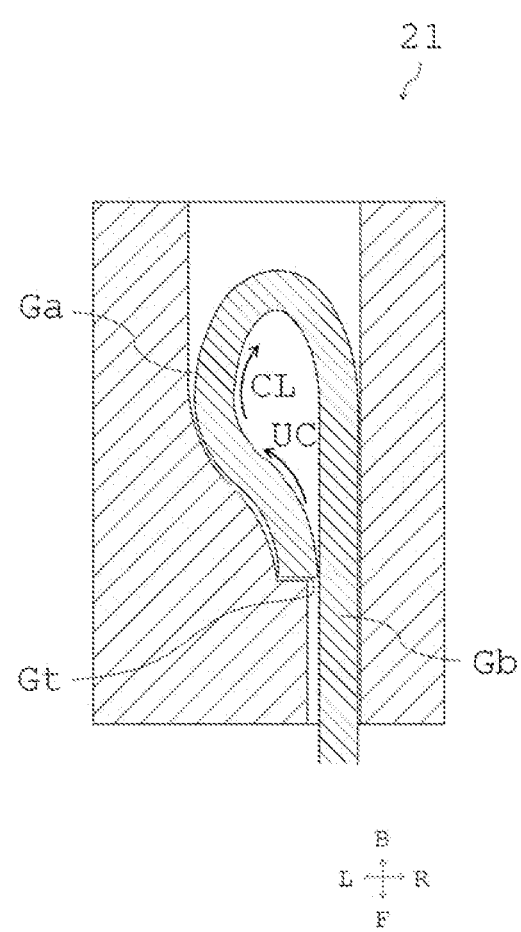
Figure 12:
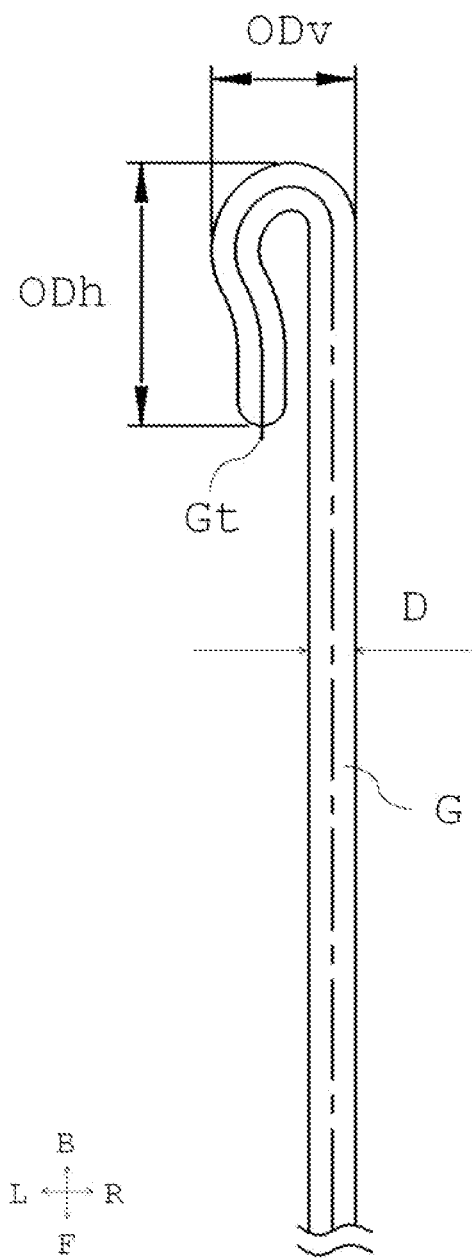
FIG. 12 shows an example of a guide wire after shaping.

FIGS. 11A, 11B, and 12 show an example of the second embodiment of the present invention. A guide wire shaping mold 21 includes a main body portion 22 and a lid portion 23. FIG. 11A is a cross-sectional view of the main body portion 22 showing a cross section similar to that in FIG. 1D. FIG. 11B shows a cross section in a state where the guide wire G is arranged in the guide wire shaping mold 21 similarly to FIG. 3B.

As shown in FIG. 11A, on the left side in the cavity, a wire shaping chamber 24 has an inner wall whose part faces substantially rightward and the other part faces rearward. In this inner wall, a rear portion in plan view is represented by a straight line in the front-rear direction, a front portion is represented by a curved line in a gentle S shape, and a portion adjacent to a wire drawing path 25 is represented by a straight line in the left-right direction. The inner wall represented by the curved line is referred to as a wire curved surface wall 24b. The inner wall adjacent to the wire drawing path 25 forms a rearward stepped portion between the wire curved surface wall 24b and the wire drawing path 25. This stepped portion is referred to as a wire curved surface stepped portion 24c.

The wire drawing path 25 has an rightward facing inner wall on the left side, and this inner wall is represented by a straight line in the front-rear direction in plan view and is referred to as a wire curved surface stepped portion adjacent wall 25b. The wire curved surface stepped portion adjacent wall 25b is continuous with the wire curved surface wall 24b via the wire curved surface stepped portion 24c in plan view.

The one end side Ga is annularly arranged in the wire shaping chamber 24 as shown in FIG. 11B. The other end side Gb is linearly arranged in the wire drawing path 5. The one end side Ga first forms a curved line in a counterclockwise direction UC rearward from the most tip end portion Gt in plan view. Next, a curved line is formed in the clockwise direction CL, and the curved state continues up to a point where the guide wire G merges with the wire planar guide wall 24a.

A guide wire shaping method 121 according to the present embodiment will be described. The flowchart is similar to the flowchart shown in FIG. 6.

Through a mold preparation process 122 and a wire insertion step 123a of a wire arrangement process 123, in a wire reinsertion step 123b, the operator performs an operation of turning the guide wire G counterclockwise using the fingers so as to reverse the orientation of the most tip end portion Gt downward. At this time, the operator bends and deforms the guide wire G along the wire curved surface wall 24b, and sends the guide wire G forward so that the most tip end portion Gt abuts on or is close to the wire curved surface stepped portion 24c.

Then, the shaped guide wire G is obtained through a wire arrangement step 123c, an annular diameter reduction process 124, and a wire taking-out process 125. According to the guide wire shaping mold 21 and the guide wire shaping method 121 of the present embodiment, the guide wire G is shaped into a shape as shown in FIG. 12. As an example, using the guide wire G having an outer diameter D of 0.36 mm shown in FIG. 12, it is possible to perform shaping in which an annular portion has an annular outer diameter ODh of 2 mm in the front-rear direction and an annular outer diameter ODv of 1.1 mm in the left-right direction.

Other configurations are common to those of the first embodiment.

As shown in the present embodiment, by changing the shape of the guide wire shaping mold, the shape of the guide wire G after shaping can be discretionarily changed.

Figure 13A:
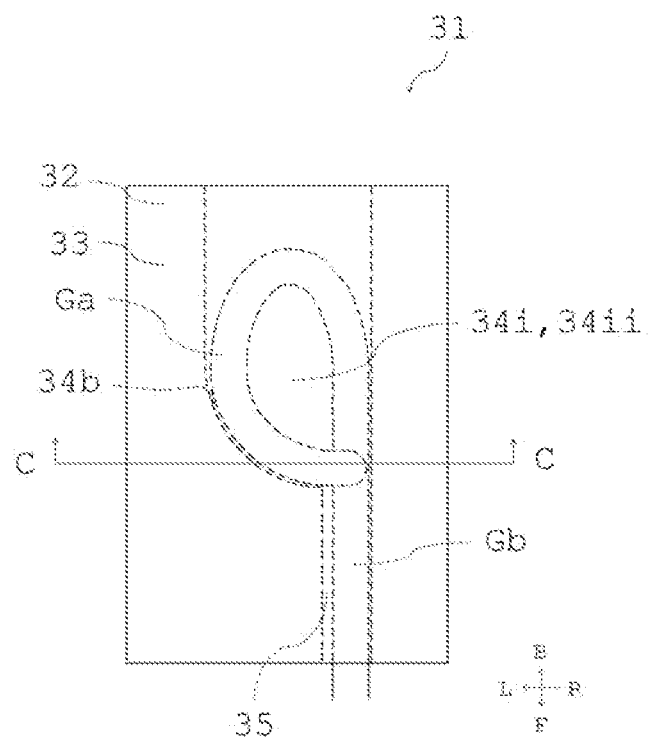
FIG. 13A shows a plan view of a guide wire shaping mold in a state where a guide wire according to a third embodiment of the present invention is arranged.
Figure 13B:
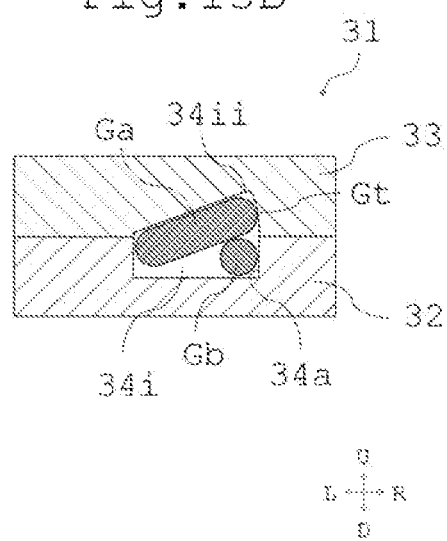
FIG. 13B shows a front cross-sectional view of the same.

FIGS. 13A and 13B show an example of the third embodiment of the present invention. In the drawing, 31 is a guide wire shaping mold, and this guide wire shaping mold 31 includes a main body portion 32 and a lid portion 33.

FIG. 13A is a plan view of a state where the guide wire G is arranged in the guide wire shaping mold 31. FIG. 13B shows a C-C cross-sectional view of the main body portion 32 and the guide wire G in which the viewing orientation is designated by the cross-section designation line of FIG. 13A.

The main body portion 32 has a recessed main body portion wire shaping chamber 34i and a wire drawing unit 35 provided downward from the up side surface. The lid portion 33 has a recessed lid portion wire shaping chamber 34ii provided upward from the down side surface. As shown in the cross-sectional view of FIG. 13B, the lid portion wire shaping chamber 34ii has a slope ceiling having a larger upward depth toward the right side. In a state where the lid portion 33 is assembled to the main body portion 32, the main body portion wire shaping chamber 34i and the lid portion wire shaping chamber 34ii are integrated to form one wire shaping chamber 34, which is a flat cavity.

The lid portion wire shaping chamber 34ii has a left facing inner wall on the right side of FIG. 13B. The inner wall of this lid portion wire shaping chamber 34ii is not positioned on the right side relative to the wire planar guide wall 34a, which is the leftward facing inner wall of the main body portion wire shaping chamber 34i.

A guide wire shaping method 131 according to the present embodiment will be described. The flowchart is similar to the flowchart shown in FIG. 6.

Through a mold preparation process 132 and a wire insertion step 133a of a wire arrangement process 133, in a wire reinsertion step 133b, the operator performs an operation of turning the guide wire G counterclockwise using the fingers so as to reverse the orientation of the most tip end portion Gt downward. At this time, the operator bends and deforms the guide wire G along the wire curved surface wall 34b, and sends the guide wire G forward so that the most tip end portion Gt reaches the deep portion of the foremost and right side of the lid portion wire shaping chamber 34ii.

Through the wire reinsertion step 133b, the most tip end portion Gt rides on the up side of the other end side Gb, and is arranged in a posture where the most tip end portion Gt is positioned up side toward the right side as shown in FIG. 13B. At this time, the left facing inner wall of the lid portion wire shaping chamber 34ii is not positioned on the right side relative to the wire planar guide wall 34a in plan view. Therefore, although the most tip end portion Gt rides on the up side of the other end side Gb, the most tip end portion Gt is blocked by the leftward inner wall of the lid portion wire shaping chamber 34ii, and does not protrude rightward relative to the right end edge of the other end side Gb in plan view.

The shaped guide wire G is obtained through an annular diameter reduction process 134 and a wire taking-out process 135. According to the guide wire shaping mold 31 and the guide wire shaping method 131 of the present embodiment, the guide wire G is shaped such that the most tip end portion Gt overlaps the up side of the other end side Gb.

Other configurations are common to those of the first embodiment.

Thus, since the most tip end portion Gt receives frictional force from the other end side Gb due to a three-dimensional structure in which the most tip end portion Gt overlaps the up side of the other end side Gb within a range in which the most tip end portion Gt does not protrude rightward, the contact state or the proximity state with the other end side Gb can be easily continued even after the wire taking-out process 135. Due to these, it is possible to more easily maintain the state where the most tip end portion Gt is folded back, and the most tip end portion Gt does not protrude rightward, and hence it is possible to reduce damage on the blood vessel caused by the guide wire G.

In FIGS. 13A and 13B, the double structure is formed in which only the most tip end portion Gt overlaps the other end side Gb. However, a spiral double structure may be formed by further advancing the most tip end portion Gt counterclockwise of FIG. 13A.

Figure 14A:
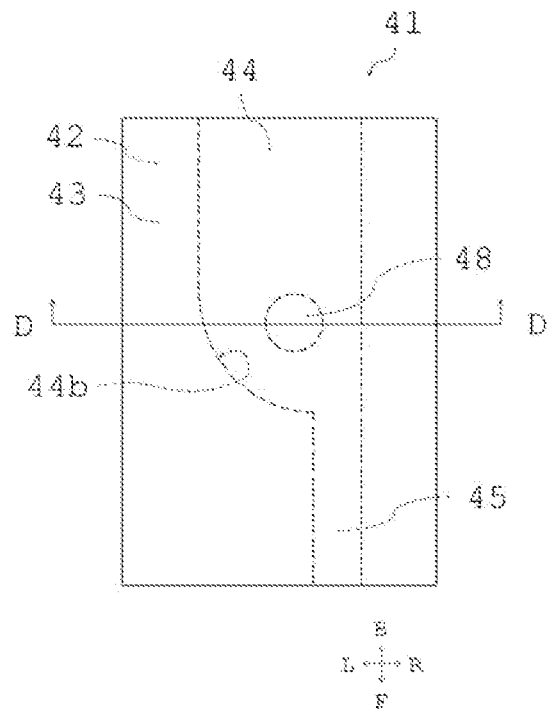
FIG. 14A shows a plan view of a guide wire shaping mold according to a fourth embodiment of the present invention.
Figure 14C:
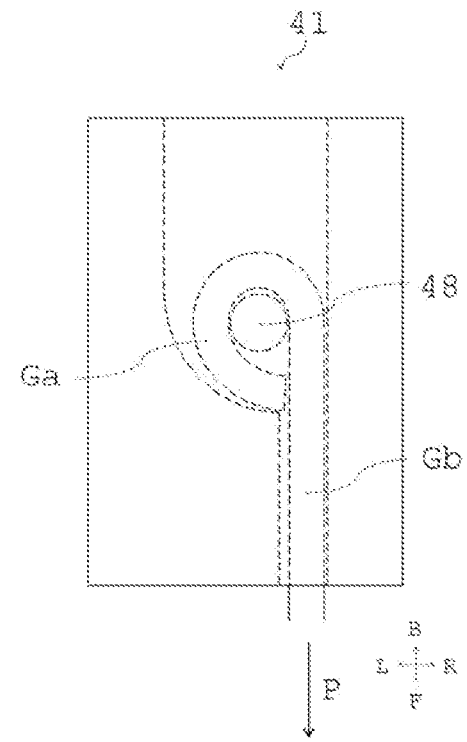
FIG. 14C shows a plan view of a guide wire shaping mold in a state where a guide wire is arranged.
Figure 14B:
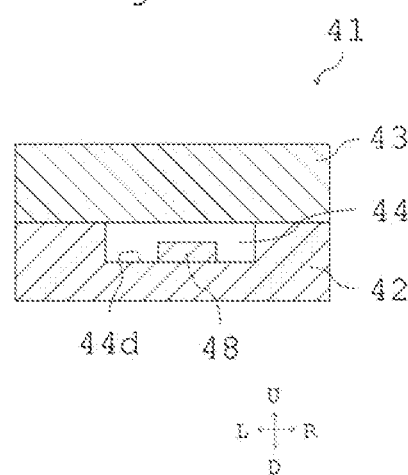
FIG. 14B shows a cross-sectional front view of the guide wire shaping mold of the same.

FIGS. 14A, 14B, and 14C show an example of the fourth embodiment of the present invention. In the drawing, 41 is a guide wire shaping mold, and this guide wire shaping mold 41 includes a main body portion 42 and a lid portion 43.

FIG. 14A is a plan view of the guide wire shaping mold 41. FIG. 14B shows a D-D cross-sectional view of the main body portion 42 and the lid portion 43 in which the viewing orientation is designated by the cross-section designation line of FIG. 14A. FIG. 14C is a plan view of a state where the guide wire G is arranged in the guide wire shaping mold 41.

The main body portion 42 includes a cylindrical projection wire guide shaft 48 that protrudes upward from a shaping chamber bottom wall 44d, which is a bottom wall of a wire shaping chamber 44.

The height of the projection wire guide shaft 48 from the shaping chamber bottom wall 44d is smaller than the height at which the projection wire guide shaft 48 abuts on the bottom surface of the lid portion 43, which is the ceiling of the wire shaping chamber 44. The center of the projection wire guide shaft 48 in plan view coincides with the center of the substantial arc of the wire curved surface wall 44b, or is positioned in the vicinity of the center of this substantial arc.

Note that the projection wire guide shaft 48 provided separately as shown in the figure may be attached to the main body portion 42, or may be provided integrally with the main body portion 42.

A guide wire shaping method 141 according to the present embodiment will be described. The flowchart is similar to the flowchart shown in FIG. 6.

In an annular diameter reduction process 144, as shown in FIG. 14C, meanwhile the guide wire G receives the tensile force P, the annular diameter of the guide wire G in the annular state is reduced while the one end side Ga is entangled with the projection wire guide shaft 48.

Since the one end side Ga is bent and deformed so as to be wound around the projection wire guide shaft 48, the annular inner diameter ID can be reduced, and can be shaped into a smaller annular state. At the same time, the annular outer diameter OD of the one end side Ga is reduced.

Other configurations are common to those of the first embodiment.

Thus, the operator can more easily reduce the annular diameter, and can perform more efficient shaping of the guide wire G.

Note that the projection wire guide shaft 48 may have a shape other than a cylindrical shape as long as the one end side Ga can be entangled when the guide wire G receives the tensile force P, and may have a shape such as a columnar shape, a polygonal columnar shape, and a pyramid shape having a cross section of an ellipse, an oval shape, a polygon shape, and the like.

The position where the projection wire guide shaft 48 is disposed may be a position other than the vicinity of the center of the substantial arc as long as the one end side Ga can be entangled. Furthermore, even when the shape of the wire curved surface wall 44b is other than a substantial arc in plan view, the projection wire guide shaft 48 is only required to be positioned near the center of the annular state of the one end side Ga where the one end side Ga can be entangled.

Moreover, the projection wire guide shaft 48 may not protrude upward from the main body portion 42, and may protrude downward from the lid portion 43 in the opposite orientation.

FIG. 15 an example of the fifth embodiment of the present invention. In the drawing, 51 is a guide wire shaping mold, and this guide wire shaping mold 51 includes a main body portion 52 and a lid portion 53.

The plan view is expressed similarly to FIGS. 14A and 14C. FIG. 15 shows a cross-sectional view of the main body portion 52 and the lid portion 53 in which the viewing orientation is designated by the cross-section designation line as in FIG. 14A. The guide wire G is arranged in the guide wire shaping mold 51 similarly to FIG. 14C.

In the main body portion 52 and the lid portion 53, a shaping chamber bottom wall 54d, which is a bottom wall of a wire shaping chamber 54, and a shaping chamber ceiling 54e, which is a part of the bottom surface of the lid portion 53 and is a ceiling of the wire shaping chamber 54 are connected by a columnar wire guide shaft 59 having a columnar shape disposed in the up-down direction.

The center of the columnar wire guide shaft 59 in plan view coincides with the center of the substantial arc of a wire curved surface wall 54b, or is positioned in the vicinity of the center of this substantial arc.

The columnar wire guide shaft 59 may be attached separately from the main body portion 52 as shown in the figure, or may be provided integrally with the main body portion 52. Furthermore, it may be provided integrally with the lid portion 53.

The height of the columnar wire guide shaft 59 from the shaping chamber bottom wall 54d coincides with the height of the wire shaping chamber 54. Therefore, when the main body portion 52 and the lid portion 53 are assembled with screws in the up-down direction not illustrated, the columnar wire guide shaft 59 is connected to the lid portion 53 with its up side surface in close contact with the shaping chamber ceiling 54e.

A guide wire shaping method 151 according to the present embodiment will be described. The flowchart is similar to the flowchart shown in FIG. 6.

In an annular diameter reduction process 154, meanwhile the guide wire G receives the tensile force P, the annular diameter of the guide wire G in the annular state is reduced while the one end side Ga is entangled with the columnar wire guide shaft 59.

Since the one end side Ga is bent and deformed so as to be wound around the columnar wire guide shaft 59, the annular inner diameter ID can be reduced, and can be shaped into a smaller annular state. At the same time, the annular outer diameter OD of the one end side Ga is reduced.

Other configurations are common to those of the first embodiment and the fourth embodiment.

Thus, the operator can more easily reduce the annular diameter, and can perform more efficient shaping of the guide wire G.

Note that the columnar wire guide shaft 59 may have a shape other than a cylindrical shape as long as the one end side Ga can be entangled when the guide wire G receives the tensile force P, and may have a shape such as a columnar shape and a polygonal columnar shape having a cross section of an ellipse, an oval shape, a polygon shape, and the like.

The position where the columnar wire guide shaft 59 is disposed may be a position other than the vicinity of the center of the substantial arc as long as the one end side Ga can be entangled similarly. Furthermore, even when the shape of the wire curved surface wall 54*b* is other than a substantial arc in plan view, the projection wire guide shaft 48 is only required to be positioned near the center of the annular state of the one end side Ga where the one end side Ga can be entangled.

The sixth embodiment of the present invention will be described with reference to FIGS. 16 to 20. In the figure, 61 denotes a guide wire shaping mold.

Figure 16A:
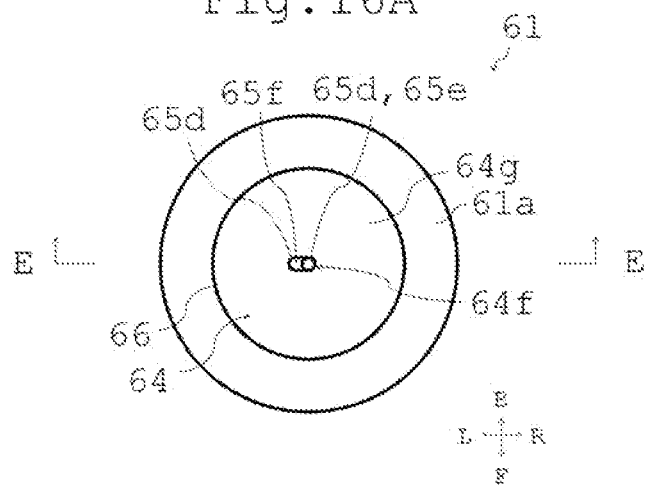
FIG. 16A shows a plan view of a guide wire shaping mold according to a sixth embodiment of the present invention.
Figure 16B:
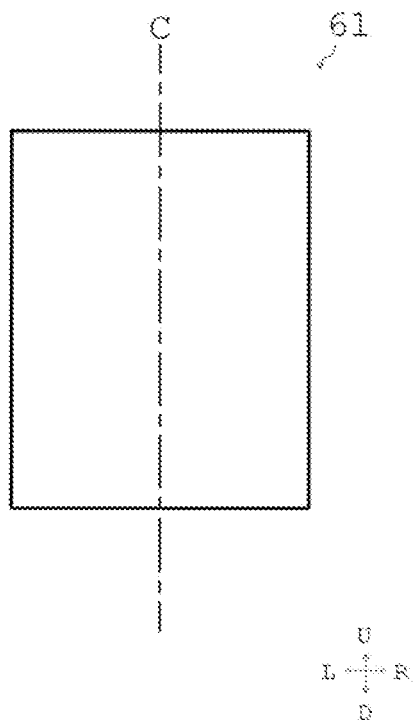
FIG. 16B shows a front view of the same.
Figure 16C:
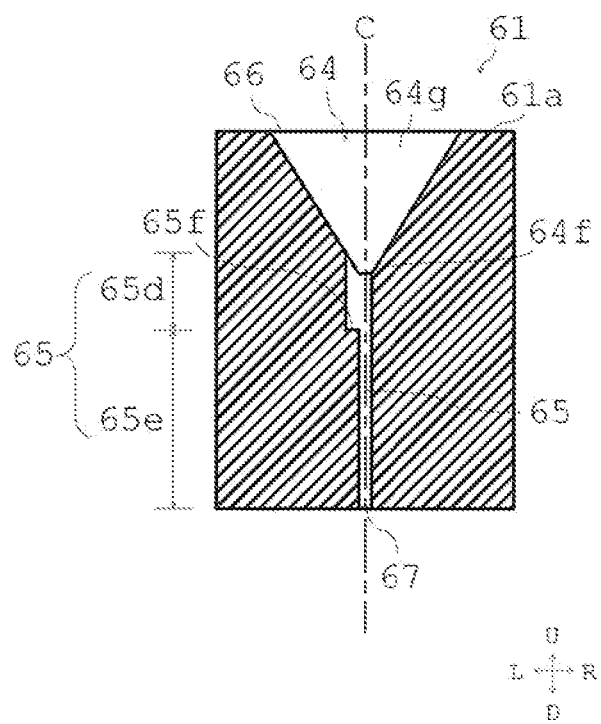
FIG. 16C shows a front cross-sectional view of a guide wire shaping mold.

In FIG. 16A, which is a plan view, an arrow F represents the forward orientation in a front-rear direction of the guide wire shaping mold 61. An arrow B represents the rearward orientation in the front-rear direction. The forward side is referred to as a front side, and the rearward side is referred to as a rear side. An arrow L represents a leftward orientation L in a left-right direction. An arrow R represents a rightward orientation R in the left-right direction. The leftward side is referred to as a left side, and the rightward side is referred to as a right side. In FIG. 16B, which is a front view, an arrow U represents an upward orientation in an up-down direction of the guide wire shaping mold 61. An arrow D represents a downward orientation in the up-down direction. The upward side is referred to as an up side, and the downward side is referred to as a down side. The same applies to other figures. FIG. 16C shows an E-E cross-sectional view of the guide wire shaping mold 61 in which the viewing orientation is designated by the cross-section designation line of FIG. 16A.

As shown in FIGS. 16A to 16C, the guide wire shaping mold 61 has an axis center C in the up-down direction and forms a columnar shape having a downward depression on an upper bottom surface 61*a*, which is an upper bottom surface. The depression of the guide wire shaping mold 61 forms a wire shaping portion 64 where the one end side Ga of the guide wire G is arranged. The guide wire shaping mold 61 has a wire drawing path 65 formed in a passage shape having a columnar space whose center line coincides with the axis center C, the wire drawing path 65 communicating downward from the wire shaping portion 64. Note that in order to simply show the structure of the guide wire shaping mold 61, the entire guide wire shaping mold 61 is expressed in a cylindrical shape, but the entire guide wire shaping mold 61 may have a shape other than the cylindrical shape as long as the shape, arrangement, and the like of the wire shaping portion 64 and the wire drawing path 65 are as shown in these figures.

The wire shaping portion 64 is a substantially inverted conical depression whose diameter is reduced downward and the depression having a shaping portion inner peripheral surface 64*g*, which is a truncated conical inner peripheral surface whose center line coincides with the axis center C of the cylinder. The circular shape corresponding to the substantially inverted conical bottom surface is smaller in diameter than the upper bottom surface 61*a*, and forms an outlet opening 66, which is an opening of the wire shaping portion 64. The outlet opening 66 opens upward, and the wire shaping portion 64 opens upward with respect to the mold outside. The wire drawing path 65 forms an outlet hole 67 opening downward and communicates with the mold outside via the outlet hole 67.

The wire shaping portion 64 communicates with the wire drawing path 65 in the front-rear direction at a truncated cone tip end portion 64*f*, which is a lower tip end portion. At this time, the shaping portion inner peripheral surface 64*g* and the inner peripheral surface of the wire drawing path 65 are continuous in the up-down direction.

The wire drawing path 65 includes a shaping portion adjacent portion 65*d*, which is a portion adjacent to the wire shaping portion 64, and a wire drawing portion 65*e* located in a lower side of the shaping portion adjacent portion 65*d*. The shaping portion adjacent portion 65*d* includes a space having an oval transverse cross section. The wire drawing portion 65*e* includes a space having a circular transverse cross section. A width of the oval in the front-rear direction coincides with the diameter of the circle, and the oval is an oval in which the circle protrudes leftward in a plan view.

The transverse cross section of the shaping portion adjacent portion 65*d* is slightly larger than a transverse cross section when two guide wires G are arranged side by side. The transverse cross section of the wire drawing portion 65*e* is slightly larger than one guide wire G. Thus, the area of the transverse cross section of the shaping portion adjacent portion 65*d* is larger than the area of the transverse cross section of the wire drawing portion 65*e*.

The shaping portion adjacent portion 65*d* and the wire drawing portion 65*e* have a step corresponding to a region in which the circle is removed from the oval in plan view. The shaping portion adjacent portion 65*d* and the wire drawing portion 65*e* have a step surface 65*f*, which is an upward facing plane in this step.

Figure 17:
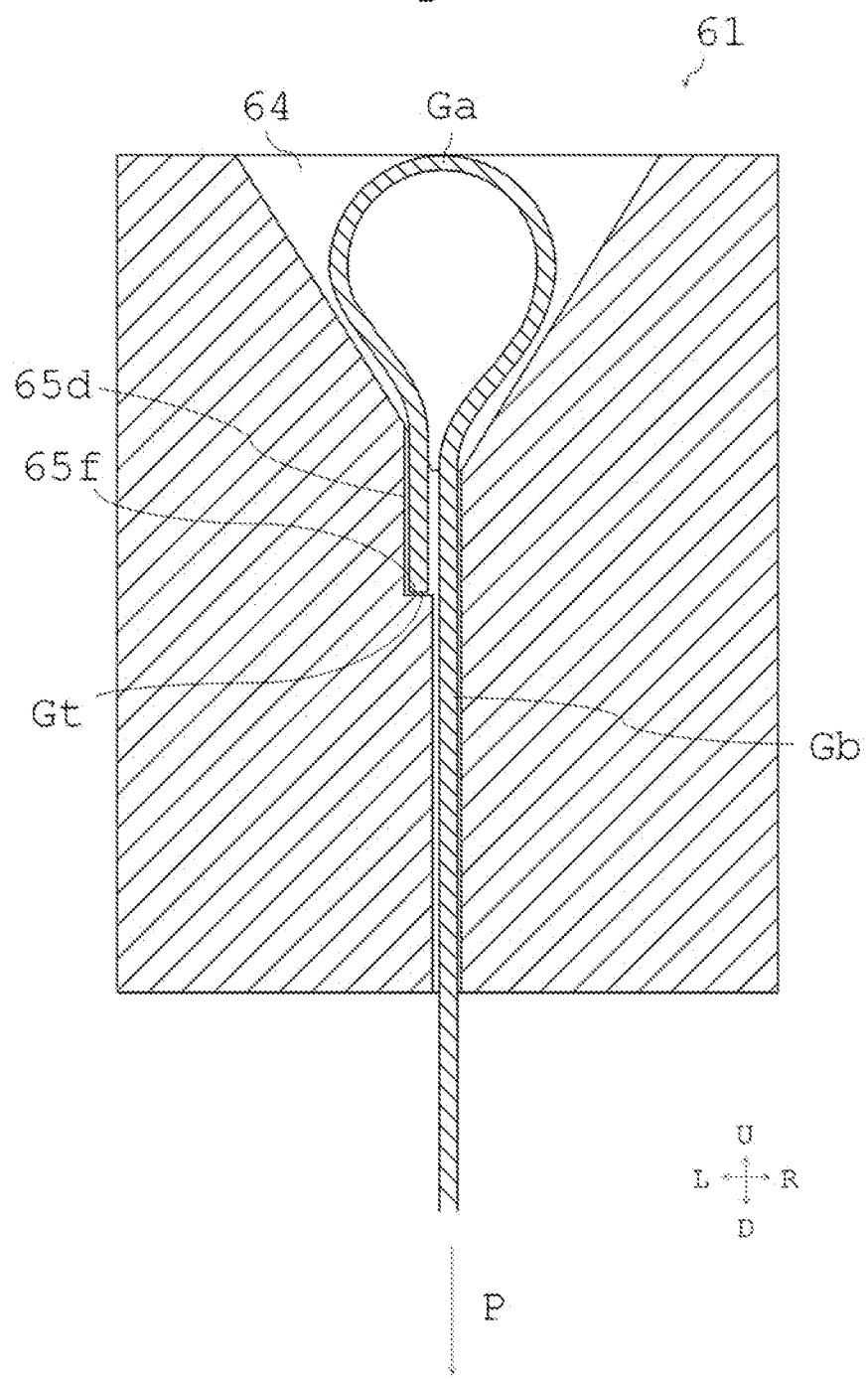
FIG. 17 shows a front cross-sectional view of a guide wire shaping mold according to the sixth embodiment in a state where a guide wire is arranged.

FIG. 17 shows an E-E cross section of the guide wire shaping mold 61 in a state where the guide wire G is arranged in which the viewing orientation is designated by the cross-section designation line of FIG. 16A. As shown in FIG. 17, in the one end side Ga of the guide wire G, the annular one end side Ga is arranged in the wire shaping portion 64, and the other end side Gb is arranged linearly in the up-down direction in the wire drawing path 65.

The most tip end portion Gt and a portion close to the most tip end portion Gt of the guide wire G are arranged in the shaping portion adjacent portion 65*d* of the wire drawing path 65. Since the shaping portion adjacent portion 65*d* can accommodate side by side two guide wires G, the other end side Gb and a portion close to the most tip end portion Gt are arranged to overlap in the shaping portion adjacent portion 65*d*. At this time, the most tip end portion Gt abuts on or gets close to the step surface 65*f*.

Here, a guide wire shaping method 161 including a procedure of shaping the guide wire G will be described. The guide wire shaping method 161 is shown in the flowchart of FIG. 6.

The guide wire shaping method 161 includes a mold preparation process 162 of preparing the guide wire shaping mold 61 first. In the mold preparation process 162, a first guide wire shaping mold block 61*b* shown in the plan view in FIG. 18A and a second guide wire shaping mold block 61*c* shown in the plan view in FIG. 18B are prepared. The first guide wire shaping mold block 61*b* and the second guide wire shaping mold block 61*c* are block bodies in which the guide wire shaping mold 61 shown in FIGS. 16A to 16C is divided into two in the left-right direction in advance on a dividing surface in the front-rear direction passing through the axis center C. That is, the first guide wire shaping mold block 61*b* corresponds to the left half of the shaping mold 61 shown in FIGS. 16A to 16C, and the second guide wire shaping mold block 61*c* corresponds to the right half of the same.

The guide wire shaping mold blocks 61*b* and 61*c* are formed by, for example, injection molding with synthetic resin such as an acrylic resin and polycarbonate as raw materials.

Each of the guide wire shaping mold blocks 61b and 61c has a dividing surface in the front-rear direction and passes through the axis center C of the guide wire shaping mold 61. Therefore, the left half of the shaping portion adjacent portion 65d and the left half of the wire drawing portion 65e are each provided leftward in a recessed manner on a first dividing surface 61d, which is a dividing surface on the first guide wire shaping mold block 61b side, and the right half of the shaping portion adjacent portion 65d and the right half of the wire drawing portion 65e are each provided rightward in a recessed manner on a second dividing surface 61e, which is a dividing surface on the second guide wire shaping mold block 61c side.

The left half of the shaping portion inner peripheral surface 64g is provided leftward in a recessed manner on the first dividing surface 61d, which is a dividing surface on the first guide wire shaping mold block 61b side, and a right half of the shaping portion inner peripheral surface 64g is provided rightward in a recessed manner on the second dividing surface 61e, which is a dividing surface on the second guide wire shaping mold block 61c side.

Thereafter, in the mold preparation process 162, the first dividing surface 61d and the second dividing surface 61e are aligned such that the left and right recessed portions thereof coincide with each other, and then the first guide wire shaping mold block 61b and the second guide wire shaping mold block 61c are assembled with screws in the left and right direction not illustrated. Then, the operator prepares the guide wire G and the assembled guide wire shaping mold 61 at hand.

After the mold preparation process 162, the guide wire shaping method 161 includes a wire arrangement process 163 of arranging the guide wire G in the guide wire shaping mold 61.

Figure 19A:
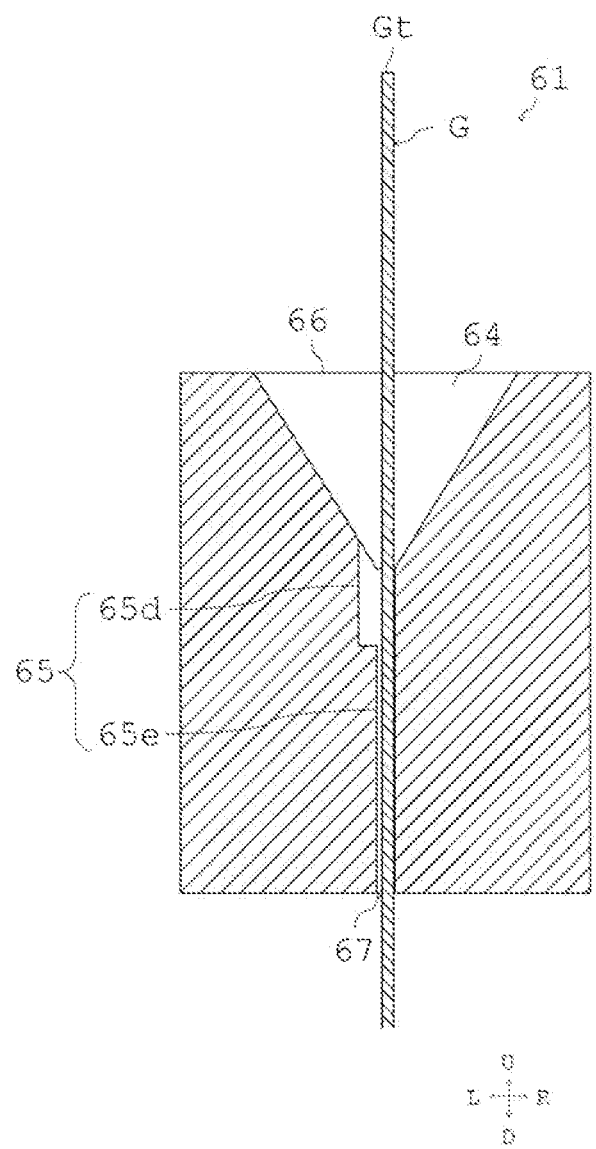
FIGS. 19A and 19B show front cross-sectional views of a guide wire and a guide wire shaping mold in a guide wire shaping method according to the sixth embodiment of the present invention.

In the wire arrangement process 163, the operator first inserts the most tip end portion Gt of the guide wire G from the outlet hole 67 using fingers, and sequentially passes upward the most tip end portion Gt through the wire drawing path 65 and the wire shaping portion 64. When passing through the wire drawing path 65, the guide wire G sequentially passes through the wire shaping portion 65e and the shaping portion adjacent portion 65d. This state is shown in FIG. 19A. The most tip end portion Gt protrudes to the mold outside through the outlet opening 66. This step is referred to as a wire insertion step 163a.

Figure 19B:
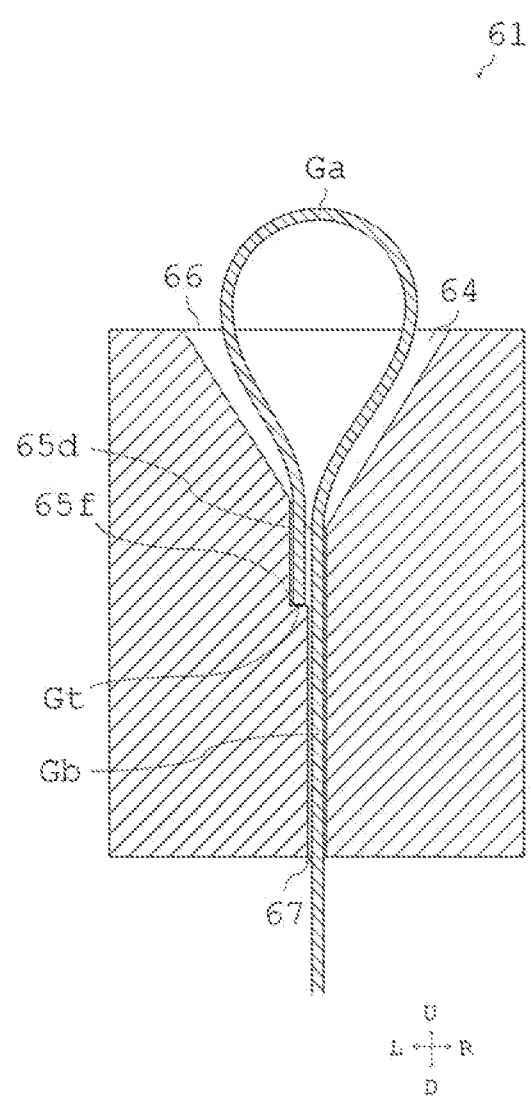

Next, in the wire arrangement process 163, the operator performs an operation of turning the guide wire G counterclockwise using the fingers so as to reverse the orientation of the most tip end portion Gt downward. Then, the operator returns the most tip end portion Gt to the wire shaping portion 64, and inserts the most tip end portion Gt downward into the shaping portion adjacent portion 65d with the most tip end portion Gt as a head and brings it into contact with the step surface 65f. As a result, as shown in FIG. 19B, the guide wire G is bent and deformed, and the portion of the guide wire G close to the most tip end portion Gt and the other end side Gb are arranged side by side in the shaping portion adjacent portion 65d. This step is referred to as a wire reinsertion step 163b.

Next to the wire reinsertion step 163b, in the wire arrangement process 163, the operator pulls the hand side of the guide wire G. As a result, as shown in FIG. 17, when the other end side Gb of the guide wire G is pulled downward from the large annular state as shown in FIG. 19B, the annular diameter of the guide wire G in this annular state is reduced and changes to a relatively small annular state.

Thus, the one end side Ga of the guide wire G is annularly arranged in the wire shaping portion 64 as in FIG. 17, and the other end side Gb is linearly arranged in the wire drawing path 65. This step is referred to as a wire arrangement step 163c.

At this time, since the wire arrangement process 163 includes the wire insertion step 163a and the wire reinsertion step 163b, it is not necessary to disassemble the guide wire shaping mold 61 into the first guide wire shaping mold block 61b and the second guide wire shaping mold block 61c for arranging the guide wire G, and the guide wire G can be arranged at a predetermined position in a state where the first guide wire shaping mold block 61b and the second guide wire shaping mold block 61c are assembled. As a result, the guide wire G can be more efficiently shaped.

Since the wire shaping portion 64 forms a substantially inverted conical depression, in the wire reinsertion step 163b, the operator can easily insert the most tip end portion Gt into the wire into the shaping portion adjacent portion 65d by putting the most tip end portion Gt along the shaping portion inner peripheral surface 64g.

Figure 20:
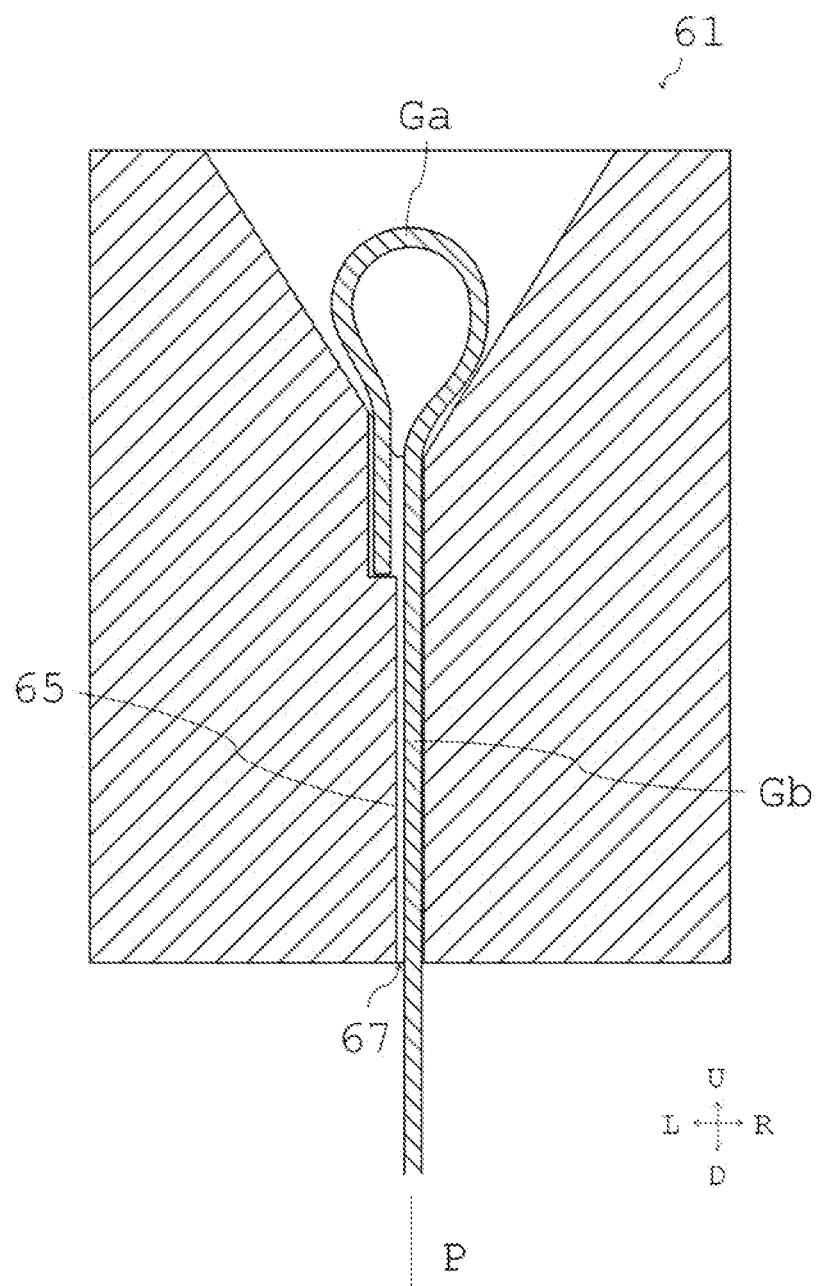
FIG. 20 shows a front cross-sectional view of the guide wire shaping mold according to the sixth embodiment in a state where the guide wire is arranged.

Next to the wire arrangement process 163, the operator further draws out a part of the other end side Gb toward the mold outside as shown in FIG. 20, shortens the entire circumference of the one end side Ga in the annular state, and reduces the annular diameter of the one end side Ga. This process is referred to as an annular diameter reduction process 164.

In the annular diameter reduction process 164, the operator pulls downward the other end side Gb exposed to the mold outside, and draws out a part of the other end side Gb remaining in the wire drawing path 65 toward the mold outside through the outlet hole 67. In this manner, the tensile force when the other end side Gb is pulled downward is indicated by an arrow P according to the orientation of pulling in FIGS. 17 and 20.

The guide wire with a safety wire, which is the guide wire G shown in FIG. 4A, and the guide wire with a plastic jacket, which is the guide wire G shown in FIG. 4B, include a core wire Gc inside in the radial direction. This core wire Gc is arranged inside a safety wire Gd or a plastic jacket Ge as shown by each transverse cross section, and each transverse cross section is formed into a substantially rectangular shape having a long side in the y direction and a short side in the x direction. Here, the long side in the y direction is referred to as an y direction long side Gy, and the short side in the x direction is referred to as an x direction short side Gx.

It is known that bending rigidity at the time of displacing the guide wire G in the y direction of the long side direction is larger than bending rigidity at the time of displacing the guide wire in the x direction, for example, when bending rigidity, which is the magnitude of resistance with respect to deformation, is compared with each other between a case of bending the guide wire such that one end is displaced in the y direction and a case of bending the guide wire such that one end is displaced in the x direction. On the contrary, it is known that bending rigidity at the time of displacing the guide wire in the x direction of the short side direction is smaller.

In this situation, in order to reduce the annular diameter of the guide wire G having such a bending characteristic, the inventor has found that when the one end portion Ga is shaped to be small using the guide wire shaping mold 61, the guide wire G changes its posture by itself, and the relationship between the y direction long side Gy of the core wire Gc and the shaping portion inner peripheral surface 64g converges to a relationship of positions parallel to each other. When the y direction long side Gy and the shaping portion inner peripheral surface 64g are parallel to each other as described above, the guide wire G is bent in the x direction, and thus the bending rigidity is relatively small. As a result, according to the guide wire shaping mold 61 of the present invention, the guide wire G can take a posture with lower bending rigidity by itself when being bent for shaping. Therefore, the operator can shape the guide wire G by applying a smaller force.

By this action, the operator can reduce the annular diameter in a posture in which the bending rigidity of the guide wire G is smaller, that is, a posture in which the guide wire is more easily bent, regardless of the orientation of the core wire Gc of the guide wire G arranged in the wire arrangement process 163. Therefore, the operator can easily shape the guide wire G by the guide wire shaping mold 61.

Through such a process, the annular diameter of the one end side Ga become smaller after pulling than that before pulling. As a result, plastic deformation occurs in a state where the one end side Ga is rounded small, and the guide wire G can be shaped into a shape reliably folded back without performing heating treatment. Due to this, it is possible to reduce damage on the blood vessel caused by the most tip end portion Gt and the one end side Ga.

The operation of reducing the annular diameter of the guide wire G by pulling the guide wire G in the wire arrangement step 163b of the wire arrangement process 163 and the operation of further reducing the annular diameter by further pulling the guide wire G in the annular diameter reduction process 164 may be continuously performed. That is, these two operations can be performed in series although the operation before the one end side Ga and the other end side Gb are arranged in the predetermined shape in FIG. 17 belongs to the wire arrangement process 163 and the operation after the same belongs to the annular diameter reduction process 164.

Next to the annular diameter reduction process 164, in order to take out the guide wire G after shaping from the guide wire shaping mold 61, the operator loosens or removes the screw in the up-down direction fastened for joining the first guide wire shaping mold block 61b and the second guide wire shaping mold block 61c in the mold preparation process 162, thereby disassembling the guide wire shaping mold 61.

This allows the operator to take out the one end side Ga and the other end side Gb in the left-right direction from the wire shaping portion 64 and the wire drawing path 65 using fingers. This process is referred to as a wire taking-out process 165. The guide wire G in a state where the one end side Ga is rounded is shaped into a desired shape through slight spring back caused by being taken out from the guide wire shaping mold 61. Then, through the wire taking-out process 165, the operator can insert the shaped guide wire G into the patient from the one end side Ga.

Although the embodiments of the present invention have been described above, the present invention is not limited to these embodiments, and various modifications can be made without departing from the gist of the present invention.

For example, the material of the guide wire shaping molds 1, 21, 31, 41, 51, and 61 may not be a synthetic resin, and a part or all of the guide wire shaping molds may be made of, for example, metal, non-metal, wood, or the like as long as they can be processed into the shapes illustrated in the drawings and have strength enough to shape the guide wire G.

The shapes of the guide wire shaping molds 1, 21, 31, 41, and 51 in the first to fifth embodiments may be reversed in left and right. That is, when the lid portions 3, 23, 33, 43, and 53 are arranged on the up sides of the main body portions 2, 22, 32, 42, and 52, the shapes of the wire shaping chambers 4, 24, 34, 44, and 54 and the wire drawing paths 5, 25, 35, 45, and 55 in plan view may be reversed between the left orientation and the right orientation.

Similarly, the wire shaping chambers 4, 24, 34, 44, and 54 and the wire drawing paths 5, 25, 35, 45, and 55 in the first to fifth embodiments may not have a recessed shape provided downward from the up side surfaces of the main body portions 2, 22, 32, 42, and 52, and may instead have a recessed shape provided upward from the down side surfaces of the lid portions 3, 23, 33, 43, and 53. Each of the main body portions 2, 22, 32, 42, and 52 and the lid portions 3, 23, 33, 43, and 53 may have a recessed portion provided downward and upward, and may be formed by a cavity and a passage in which the recessed portions are put together.

Similarly, the wire drawing paths 5, 25, 35, 45, and 55 in the first to fifth embodiments may have a shape other than the rectangular parallelepiped shape shown in the figures, and may have a shape of a tubular path having a circular cross section, for example, as long as they can guide the guide wire G. They may have a shape other than the shape provided inside the guide wire shaping molds 1, 21, 31, 41, and 51 as shown in each embodiment, and may have a pipe protruding from the guide wire shaping molds 1, 21, 31, 41, and 51 toward the model outside, for example.

The main body portions 2, 22, 32, 42, and 52 and the lid portions 3, 23, 33, 43, and 53 or the first guide wire shaping mold block 61b and the second guide wire shaping mold block 61c may not be assembled with screws, and may be assembled with clips, clamps, or the like as long as they can be firmly and detachably connected.

A plurality of the wire shaping chambers 4, 24, 34, 44, and 54, a plurality of the wire drawing paths 5, 25, 35, 45, 55, and 65, or a plurality of the wire shaping portion 64 in the sixth embodiment may be provided for one guide wire shaping molds 1, 21, 31, 41, 51, and 61.

FIG. 9(a) or FIG. 12 show the outer diameter D value, the annular outer diameter ODh value in the front-rear direction, and the annular outer diameter ODv value in the left-right direction of the guide wire G of each one example. However, values other than these values may be used as long as they are appropriate values that can reduce the annular diameter of the guide wire G and cause plastic deformation for shaping.

The dividing surfaces 61d and 61e of the first guide wire shaping mold block 61b and the second guide wire shaping mold block 61c in the sixth embodiment may not be surfaces that pass through, in the front-rear direction, the axis center C of the guide wire shaping mold 61 before division, and may be dividing boundaries of other angles, positions, shapes, and the like, such as surfaces in the left-right direction, as long as the one end side Ga and the other end side Gb can be easily taken out from the wire shaping portion 64 and the wire drawing path 65 in the wire taking-out process 165.

INDUSTRIAL APPLICABILITY

The present invention can be used for a guide wire shaping mold and a guide wire shaping method that can shape a guide wire.

REFERENCE SIGNS LIST 1, 21, 31, 41, 51, 61 guide wire shaping mold
61a upper bottom surface
61b first guide wire shaping mold block
61c second guide wire shaping mold block
2, 22, 32, 42, 52 main body portion
3, 23, 33, 43, 53 lid portion
4, 24, 34, 44, 54 wire shaping chamber (wire shaping portion)
64 wire shaping portion
4a, 24a, 34a, 44a, 55a wire planar guide wall
4b, 24b, 34b, 44b, 55b wire curved surface wall
24c wire curved surface stepped portion
44d, 54d shaping chamber bottom wall
54e shaping chamber ceiling
64f truncated cone tip end portion
64g shaping portion inner peripheral surface
5, 25, 35, 45, 55, 65 wire drawing path
5a, 25a, 35a, 45a, 55a wire planar guide extension wall
5b, 35b, 45b, 55b wire curved surface adjacent wall
25b wire curved surface stepped portion adjacent wall
65d shaping portion adjacent portion
65e wire drawing portion
65f step surface
6, 26, 36, 46, 56 outlet slit
66 outlet opening
7, 27, 37, 47, 57, 67 outlet hole
48 projection wire guide shaft
59 columnar wire guide shaft
111 to 161 guide wire shaping method
112 to 162 mold preparation process
113 to 163 wire arrangement process
113a to 163a wire insertion step
113b to 163b wire reinsertion step
113c to 163c wire arrangement step
114 to 164 annular diameter reduction process
115 to 165 wire taking-out process

The invention claimed is:

1. A guide wire shaping mold configured to shape a guide wire by reducing an annular diameter of the guide wire in which a tip end is annularly arranged, the guide wire shaping mold comprising:
a wire shaping portion configured such that an annular portion of the guide wire is arranged; and
a wire drawing path formed in a passage way shape, communicating with the wire shaping portion, and configured to retract the guide wire in a linear direction and in a base end direction.

2. The guide wire shaping mold according to claim 1, wherein at least a part of a constituent member is made of a synthetic resin.

3. The guide wire shaping mold according to claim 2, wherein the wire shaping portion is configured by a wire shaping chamber that forms a flat cavity wider than a width of the wire drawing path.

4. The guide wire shaping mold according to claim 3, wherein in the wire shaping chamber, a part of an inner wall constitutes a wire planar guide wall having a substantially planar shape, and the wire planar guide wall and a passage wall of the wire drawing path are continuous in a same plane shape.

5. The guide wire shaping mold according to claim 4, wherein in the wire shaping chamber, a part of an inner wall constitutes a wire curved surface guide wall having a curved surface shape, and the wire curved surface guide wall and a passage wall of the wire drawing path are continuous on a side opposite to a side continuous in the same plane shape.

6. The guide wire shaping mold according to claim 3, wherein the wire shaping chamber has a projection wire guide shaft in which any or both of a pair of inner walls facing each other in a thickness direction of the flat shape are provided in the thickness direction.

7. The guide wire shaping mold according to claim 3, wherein the wire shaping chamber has a columnar wire guide shaft connected to both of a pair of inner walls facing each other in a thickness direction of the flat shape.

8. The guide wire shaping mold according to claim 3, comprising:
a main body portion on one side and a lid portion on an other side configured to cover the main body portion, into which the guide wire shaping mold is divided into two in a thickness direction of a flat shape of the wire shaping chamber, wherein
a part of a bottom surface of the lid portion forms a ceiling of the wire shaping chamber.

9. The guide wire shaping mold according to claim 1, wherein
the wire shaping portion has an inner peripheral surface of a truncated cone shape, and
the wire drawing path communicates with the wire shaping portion at a tip end portion of the truncated cone shape.

10. The guide wire shaping mold according to claim 9, wherein in the wire drawing path, a cross section of a shaping portion adjacent portion, which is a portion adjacent to the wire shaping portion, has a shape and an area in which two of the guide wires are arranged in an overlapping manner, the wire drawing path has the shaping portion adjacent portion and a wire drawing portion, which is a portion continuous with the shaping portion adjacent portion in an orientation away from the wire shaping portion and having a cross-sectional area smaller than a cross-sectional area of the shaping portion adjacent portion, and has a step surface facing an orientation approaching the wire shaping portion in a step between the shaping portion adjacent portion and the wire drawing portion.

11. A guide wire shaping method comprising:
a mold preparation process of preparing a guide wire shaping mold including a wire drawing path formed in a passage shape and a wire shaping portion including a shaping space that communicates with the wire drawing path;
a wire arrangement process of inserting a guide wire from an outlet hole of the wire drawing path and annularly arranging a tip end of the guide wire in the wire shaping portion; and
an annular diameter reduction process of drawing out a base end side of the guide wire from the outlet hole and shortening an entire circumference of an annular portion on the tip end side to reduce an annular diameter of the annular portion.

12. The guide wire shaping method according to claim 11, wherein
in the guide wire shaping mold prepared in the mold preparation process, the wire shaping portion is opened to a wire outside of the guide wire shaping mold, and
the wire arrangement process includes a wire insertion step of causing a tip end of the guide wire inserted from the outlet hole to protrude to the mold outside through the wire shaping portion, and a wire reinsertion step, which is a step of reversing an orientation and returning to the wire shaping portion again.

\* \* \* \* \*